US006342483B1

(12) United States Patent
Holt et al.

(10) Patent No.: US 6,342,483 B1
(45) Date of Patent: Jan. 29, 2002

(54) METHOD FOR DETECTION AND TREATMENT OF BREAST CANCER

(75) Inventors: Jeffrey T. Holt, Brentwood; Roy A. Jensen, Franklin; David L. Page, Nashville; Patrice S. Obermiller, Nashville; Cheryl L. Robinson-Benion, Nashville; Marilyn E. Thompson, Nashville, all of TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/007,678

(22) Filed: Jan. 15, 1998

Related U.S. Application Data

(63) Continuation of application No. 08/373,799, filed on Jan. 17, 1995, now abandoned, which is a continuation-in-part of application No. 08/182,961, filed on Jan. 14, 1994, now Pat. No. 5,677,125.

(51) Int. Cl.[7] .................. A61K 48/00; C12N 15/63; C12N 15/86; C12N 5/00
(52) U.S. Cl. .................. 514/44; 435/455; 435/456; 435/320.1; 435/375
(58) Field of Search .................. 514/44; 435/320.1, 435/455–458, 375

(56) References Cited

U.S. PATENT DOCUMENTS

| 5,693,473 A | * | 12/1997 | Shattuck-Eidens et al. ..... 435/6 |
| 5,709,999 A | * | 1/1998 | Shattuck-Eidens et al. ..... 435/6 |
| 5,710,001 A | * | 1/1998 | Skolnick et al. ................ 435/6 |
| 5,747,282 A | * | 5/1998 | Skolnick et al. ............ 435/69.1 |
| 5,753,441 A | * | 5/1998 | Skolnick et al. ................ 435/6 |

FOREIGN PATENT DOCUMENTS

| EP | 0 699 754 A1 | 3/1996 | ............ C12N/15/12 |
| EP | 0 705 902 A1 | 4/1996 | ............ C12N/15/12 |
| EP | 0 705 903 A1 | 4/1996 | ............ C12N/15/12 |
| WO | WO 95/25429 | 9/1995 | ............ C07K/14/82 |
| WO | WO 95/25813 | 9/1995 | ............ C12Q/1/68 |
| WO | WO 96/05306 | 2/1996 | ............ C07K/14/82 |
| WO | WO 96/05307 | 2/1996 | ............ C07K/14/82 |
| WO | WO 96/05308 | 2/1996 | ............ C07K/14/82 |

OTHER PUBLICATIONS

Yue et al., "A New Nude Mouse Model for Postmenopausal Breast Cancer using MCF–7 Cells Transfected with the Human Aromatase Gene," Cancer Research, vol. 54 (No. 19), pp. 5092–5095, (Oct. 1, 1994).
Arteaga et al., "Tissue–Targeted Antisense c–fos Retroviral Vector Inhibits Established Breast Cancer Xenografts in Nude Mice," Cancer Research, vol. 56 (Nov. 5), pp. 1098–1103, (Mar. 1, 1996).
Tait et al., "A Phase I Trial of Retroviral BRCA1sv Gene Therapy in Ovarian Cancer," Clinical Cancer Research, vol. 3 (No. 11), pp. 1959–1968 (Nov. 1997).
Lawrence H. Arp, "Tumor Models: Assessing Toxicity in Efficacy Studies," Toxicologic Pathology, vol. 27 (No. 1), pp. 121–122, (Jan.–Feb. 1999).
Mc Bibby, "Making the Most of Rodent Tumour Systems in Cancer Drug Discovery," British Journal of Cancer, vol. 79 (No. 11–12), pp. 1633–1640, (1999).
Steele et al., "Preclinical Drug Development Paradigms for Chemopreventives," Hematology/Oncology Clinics of North America, vol. 12 (no. 5), pp. 943–961, (Oct. 1998).
Lopez et al., "A Model–Based Approach for Assessing in Vivo Combination Therapy Interactions," PNAS, vol. 96 (No. 23), pp. 13023–1302, (Nov. 9, 1999).
Rebecca H. Buckley, "Gene Therapy for Human SCID: Dreams become Reality," Nature Medicine, vol. 6 (No. 6), pp. 623–624, (Jun. 2000).
Roger Dobson, "Gene Therapy Saves Immune Deficient Babies in France," BMJ, vol. 320, p. 1225, (May. 6, 2000)
Cavazzana–Calvo et al., "Gene Therapy of Human Severe Combined Immunodeficiency (SCID)–XI Disease," Science, vol. 288 (No. 546), pp. 669–672, (Apr. 28, 2000).
Khuri et al., "A Controlled Trial of Intratumoral ONYX–015, a Selectively–Replicating Adenovirus, in Combination with Cisplatin and 5–Fluorouracil in Patients with Recurrent Head and Neck Cancer," Nature Medicine, vol. 6 (No. 8), pp. 879–885, (Aug. 2000).
Hall et al., "Linkage of Early Onset–Familial Breast Cancer to Chromosome 17q21," Science 250: 1684–89 (1990).
Helzouer et al., "Epidemiology, prevention, and early detection of breast cancer," Current Opinion in Oncology 7: 489–95 (1995).
Weber et al., "Familial Breast Cancer–Approaching the Isolation of Susceptibility Gene," Cancer (Supp.) 74: 1013–20 (1994).
Norris et al., "Identification of a New Subclass of Ala DNA Repeats Which Can Function as Estrogen Receptor–dependent Transcriptional Enhancers," Journal of Biological Chemistry 39:22, 777–82 (1995).

(List continued on next page.)

Primary Examiner—Dave T. Nguyen
Assistant Examiner—Quang Nguyen
(74) Attorney, Agent, or Firm—Jenkins & Wilson, P.A.

(57) ABSTRACT

The present invention provides a method of detecting and diagnosing pre-invasive breast cancer by identifying differentially expressed genes in early, pre-invasive breast cancer tissue. Differentially expressed genes can be used as genetic markers to indicate the presence of pre-invasive cancerous tissues. Microscopically-directed tissue sampling techniques combined with differential display or differential screening of cDNA libraries are used to determine differential expression of genes in the early stages of breast cancer. Differential expression of genes in preinvasive breast cancer tissue is confirmed by RT-PCR, nuclease protection assays and in-situ hybridization of ductal carcinoma in situ tissue RNA and control tissue RNA. The present invention also provides a method of screening for compounds that induce expression of the BRCA1 gene, whose product negatively regulates cell growth in both normal and malignant mammary epithlial cells. The present invention also relates to gene therapy method using this gene.

4 Claims, 20 Drawing Sheets

OTHER PUBLICATIONS

Steeg, P., "Granin expectations in breast cancer?," *Nature Genetics* 12:223–225 (1996).

Lemoine, N.R., "Molecular biology of Breast Cancer," *Annals of Oncology* 5 (Supp. 4):S31–S37 (1994).

Szabo et al., "Inherited breast and ovarian cancer," *Human Molecular Genetics* 4:1811–17 (1995).

Easton et al., "Inherited Susceptability to Breast Cancer," *Cancer Surveys* 18:95–113 (1993).

Narod, S. A., "Genetics of breast and ovarian cancer," *British Medical Bulletin* 50:656–76 (1994).

Hopkin, K., "MTSI, Telomerase May Be New Target For Cancer Therapy," *The Journal of NIH Research* 6:38–42 (1994).

Burtness, B.A., "Oncology and Hematology," *JAMA* 273:1702–1703 (1995).

Takahashi, H., "Mutation analysis of the BRCA1 gene in ovarian cancers," *Cancer Res.* 55:2998–3002 (1995).

Miki et al., "A Strong Candidate for the Breast and Ovarian Cancer Susceptibility Gene BRCA1," *Science* 266:66–71 (Oct. 7, 1994).

Narod et al., "An Evaluation of Genetic Heterogeneity in 145 Breast–Ovarian Cancer Families," *Am. J. Hum. Genet.* 56:254–264 (1995).

Campbell et al., "A Novel Gene Encoding a B–Box Protein Within the BRCA1 Region at 17q21.1," *Human Molecular Genetics* 3, No. 4: 589–594 (1994).

Marcus et al., "Pathology and Heredity of Breast Cancer in Younger Women," *Journal of the National Cancer Institute Monographs* 16:23–33 (1994).

Porter et al., "Breast Cancer Incidence, Penetrance and Survival in Probable Carriers of BRCA1 Gene Mutation in Families Linked to BRCA1 on Chromosome 17q12–21," *British Journal of Surgery* 81: 1512–1515 (1994).

Merlo et al., "Evidence for a Second Tumor Suppressor Gene on 17p Linked to High S–Phase Index in Primary Human Breast Carcinomas," *Cancer Genet Cytogenet* 76: 106–111 (1994).

Neuhausen et al., "Loss of Heterozygosity in Familial Tumors from Three BRCA1–linked Kindreds," *Cancer Research* 54:6069–6072 (1994).

Brown et al., "Regulation of BRCA1," *Nature* 372: 733 (1994).

Simard et al., "Common Origins of BRCA1 Mutations in Canadian Breast and Ovarian Cancer Families," *Nature Genetics* 8: 392–398 (1994).

Friedman et al., "Confirmation of BRCA1 by Analysis of Germline Mutations Linked to Breast and Ovarian Cancer in Ten Families," *Nature Genetics* pp. 1–6.

Castilla et al., "Mutations in the BRCA1 Gene in Families with Early–Onset Breast and Ovarian Cancer," *Nature Genetics* 8: 387–391 (1994).

Futreal et al., "BRCA1 Mutations in Primary Breast and Ovarian Carcinomas," *Science* 266:120–122 (1994).

Vieweg, J. & Gilboa, E. Considerations for the use of cytokine–secreting tumor cell preparations for cancer treatment. Cancer Invest. 13:193–201, 1995.*

Dang, C.V. et al. Gene therapy and translational cancer reserarch. Clin. Cancer Res. 5:471–474, 1999.*

Eck, S. L. & Wilson, J. M. Gene–based therapy in Goodman & Gilman's The pharmacological basis of therapeutics, Ninth edition, pp. 77–101, 1996.*

Tait et al. Ovarian cancer BRCA1 gene therapy: Phase I and II trial differences in immune response and vector stability. Clin. Cancer Res. 5:1708–1714, 1999.*

Ghebranious, N. & Donehower, L.A. Mouse models in tumor suppression. Oncogene 17:3385–3400, 1998.*

Lazennec, G et al., Expression of human estrogen receptor using an efficient adenoviral gene delivery system is able to restore hormone–dependent features to estrogen receptor–negative breast carcinoma cells. Mol. Cel. Endocrinol. 149:93–105, 1999.*

* cited by examiner

Figure 1:

Table I: Anatomic Lesion Types in the Human Breast with Pre-malignant Implication

| Pre-malignant Lesions | Relative Risk* | p value | Reference |
|---|---|---|---|
| Indicators of generalized increased risk | | | |
| Atypical ductal hyperplasia | 4-5 fold | <0.00001 | (Dupont, et al, 1985 and 1993 |
| Lobular CIS | 9-10 fold | <0.00001 | Page, et al, 1991 |
| Determinant Lesions with Regional Risk | | | |
| Non-comedo DCIS | 10-11 fold | <0.00005 | Page, et al, 1991 |

* Represents the 95% confidence interval for relative risk.

Figure 6  Comparison of the sequence between DCIS-1 [SEQ ID NO: 1] and the human and hamster genes.

```
Human     TTCTCCTGACCACTAATGGGAGCCAATTCACAATTCAC
(SEQ ID NO: 56)    ||| |||||| ||||| ||| ||  |||  |||
Hamster   TTCTGTTCACCACTGATGGCAGCTAATGAA-AATGC--
(SEQ ID NO: 58)

Human     TAAGTGACTAAAAGTAAGTTAAACTTGTGTAGACTAAGCAT
(SEQ ID NO: 57)   ||||||||||| |  |||||      |||||     |||||
Hamster   -AAGTGACTCAG--AAGTTA----GTGTT-----AGCAT
(SEQ ID NO: 59)

DCIS-1    GGGGGATCCACTAGTTC-AGAGCAGGCCCGCCACCCG
(SEQ ID NO: 1)    |||||||||||||||||  |||||||||| ||||||||
Hamster   GGGGGATCCACTAGTTCTAGAGCGG-CCGCCACCGC
(SEQ ID NO: 60)

DCIS-1    TAGGACTCCAGCTTTTGTTCCCTCTAGTGAAGGGTTAA
(SEQ ID NO: 1)    | |||||||||||| ||||||||| ||||||  |||||||
Hamster   TGGAGCTCCAGCTTTTGTTCCCTTAGTGA-GGGTTAA
(SEQ ID NO: 61)
```

Figure 8: Table 2- the Genetic Code

| Amino Acid | | | Codons | | | | |
|---|---|---|---|---|---|---|---|
| Alanine | Ala | A | GCA | GCC | GGG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG CGU |
| Serine | Ser | S | AGC | AGU | UCA | UCC | UCG UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | T | UAC | UAU | | | |

FIGURE 9-1

SEQ ID NO: 1: (DCIS-1)
TTGGGAATTG GGTACGGCGGG CCCCCACTG TGCCGAATTC CTGCATGCGG   50
GGGATCCACT AGTTCAGAGC CCGTAGGACT CCAGCTTTTG TTCGTTCCCT  100
TTAGTGAGGG TTAATTTTCG AGCTTGGGCGT AATCATGGTC ATCCTGTGTG  150
AAATTGTTAT CCGCTCACAA TTCCACACAA CATACGAGCC GGAAGCATAA  200
AAGTGTAAGC AATGAGTGAG CTAACTCACA TTAA                   234

SEQ ID NO: 2: (DCIS-2)
TAGCCCGGTT ATCGAAATAG CCACAGCGCC TCTTCACTAT CAGCAGTACG   50
CCGCCCAGTT GTACGGACAC GG                                72

SEQ ID NO: 3: (DCIS-3)
TGCCCGATGA GTTGTGTCGT ACAACTGGCG CTGTGGCTGA TTTCGATAA    49

FIGURE 9-2

SEQ ID NO: 4: (DCIS-4)
TAGCCCATGA GTTCGTGTCC GTACAACTGG GGCGCTGTGG CTGATTCGA 50
TANNNNNAGC ATCAGCCCGA CG 72

SEQ ID NO: 5: (DCIS-5)
TAGCCCGGTT ATCGAAATCA GCCACAGCGC CTAACTTCTG CAGAAGCCTT 50
TGACCATCAC CAGTTGTACG GAAACGAACT CATC 84

SEQ ID NO: 6: (DCIS-6)
GTGGTTTCCG AAATTCCTGG GAAGGGGGT GCTGGCGTGT GGAATTGTCG 50
CGGCCCCTGG TCTGCCGCGG CGTTTTTTGT CTACATTCGT CGTAGCTC 98

SEQ ID NO: 7: (DCIS-7)
ATCAGCGGCG GACATTCGGG TACCCGCGCC C*****TCCG TCGGAATTCC 50
TCGAGCCCGGG AT**ATAGGA TGTGGAGTTA GTTTTGTT 88

METHOD FOR DETECTION AND TREATMENT OF BREAST CANCER

This is a continuation application Ser. No. 08/373,799, filed Jan. 17, 1995, abandoned, which is a CIP of Ser. No. 08/182,961, filed Jan. 14, 1994, now U.S. Pat. No. 5,677,125.

The owner of this application and the parent application, Vanderbilt University, claims benefit of the Statement Verifying Small Entity Status—Non-Profit Organization filed in the parent application, as such status is still proper.

This invention was made in part from government support under Grant No. FS-00267 from the National Institutes of Health, National Institute of Environmental Health Sciences. The government has certain rights in the invention.

This is a continuation application of U.S. Pat. application Ser. No. 08/373/799, filed Jan. 17, 1995, abandoned.

UTILITY STATEMENT

The detection of differentially expressed genes in pre-invasive breast tissue, specifically in non-comedo ductal carcinoma in situ as compared to genes expressed in normal tissue, is useful in the diagnosis, prognosis and treatment of human breast cancer. Such differentially expressed genes are effective marker genes indicating the significantly increased risk of breast cancer in a patient expressing these differentially expressed marker genes. These marker genes are useful in the detection, early diagnosis, and treatment of breast cancer in humans.

The discovery of the function of the BRCA 1 gene has broad utility including, in the present invention, development of methods to treat familial and sporadic breast cancers as well as screen for therapeutic drugs through production of important indicator compounds.

ACTIVITY STATEMENT

Of the differentially expressed genes described in this invention, DCIS-1 encodes a gene similar to the M2 subunit of hamster ribonucleotide reductase. The M2 subunit of ribonucleotide reductase (RibRed, hereafter) is responsible for regulation of RibRed. The differential levels of expression of the marker genes described in this invention (Seq ID No.s 1–7), indicate genetic changes which have been linked to the presence of pre-invasive breast cancer.

The BRCA1 gene (Seq. ID No. 47) is differentially expressed in invasive breast cancer cells. The BRCA1 gene product is a negative regulator of mammary cell proliferation which is expressed at diminished levels in sporadic breast cancer.

BACKGROUND OF THE INVENTION

1. Technical Field

The present invention relates generally to methods of detection and diagnosis of breast cancer and more particularly to a diagnostic method which relies on the identification of marker genes expressed in pre-invasive cancers by microscopically-directed cloning. Furthermore, this invention concerns the prevention, detection, and diagnosis of breast cancer by addressing the molecular events which occur during the earliest alterations in breast tissue.

The present invention also relates generally to methods of treatment of breast cancer, and more particularly to gene therapy methods and methods for screening compounds that induce expression of the BRCA1 gene product.

2. Description of the Prior Art

It will be appreciated by those skilled in the art that there exists a need for a more sensitive and less invasive method of early detection and diagnosis of breast cancer than those methods currently in use. Breast cancer presents inherent difficulties in regard to the ease with which it is detected and diagnosed. This is in contrast to detection of some other common cancers, including skin and cervical cancers, the latter of which is based on cytomorphologic screening techniques.

There have been several attempts to develop improved methods of breast cancer detection and diagnosis. In the attempts to improve methods of detection and diagnosis of breast cancer, numerous studies have searched for oncogene mutations, gene amplification, and loss of heterozygosity in invasive breast cancer (Callahan, et al., 1992; Cheickh, et al., 1992; Chen, et al, 1992; and, Lippman, et al, 1990). However, few studies of breast cancer have analyzed gene mutations and/or altered gene expression in ductal carcinoma in situ (DCIS). Investigators have demonstrated high levels of p53 protein in 13–40% of DCIS lesions employing a monoclonal antibody to p53, and subsequent sequencing demonstrated mutations in several cases (Poller et al, 1992). The neu/erbB2 gene appears to be amplified in a subset of DCIS lesions (Allred et al, 1992; Maguire et al, 1992). Histologic analysis of DCIS cases suggests that mutations and altered gene expression events, as well as changes in chromatin and DNA content, occur predominantly in comedo DCIS (Böcker et al, 1992; Killeen et al, 1991; and, Komitowski et al, 1990), which has a rapid rate of local invasion and progression to metastasis. Thus, there are presently no reliable marker genes for non-comedo DCIS (NCDCIS, hereafter).

Cancer in humans appears to be a multi-step process which involves progression from pre-malignant to malignant to metastatic disease which ultimately kills the patient. Epidemiologic studies in humans have established that certain pathologic conditions are "pre-malignant" because they are associated with increased risk of malignancy. There is precedent for detecting and eliminating pre-invasive lesions as a cancer prevention strategy: dysplasia and carcinoma in-situ of the uterine cervix are examples of pre-malignancies which have been successfully employed in the prevention of cervical cancer by cytologic screening methods. Unfortunately, because the breast cannot be sampled as readily as cervix, the development of screening methods for breast pre-malignancy involves more complex approaches than cytomorphologic screening now currently employed to detect cervical cancer.

Pre-malignant breast disease is also characterized by an apparent morphological progression from atypical hyperplasias, to carcinoma in-situ (pre-invasive cancer) to invasive cancer which ultimately spreads and metastasizes resulting in the death of the patient. Careful histologic examination of breast biopsies has demonstrated intermediate stages which have acquired some of these characteristics but not others. Detailed epidemiological studies have established that different morphologic lesions progress at different rates, varying from atypical hyperplasia (with a low risk) to comedo ductal carcinoma-in-situ which progresses to invasive cancer in a high percentage of patients (London et al, 1991; Page et al, 1982; Page et al, 1985; Page et al, 1991; and Page et al, 1978). Family history is also an important risk factor in the development of breast cancer and increases the relative risk of these pre-malignant lesions (Dupont et al, 1985; Dupont et al, 1993; and, London et al, 1991). Of particular interest is non-comedo carcinoma-in-situ which is associated with a greater than ten-fold increased relative risk of breast cancer compared to control groups (Ottesen et al, 1992; Page et al, 1982). Two other reasons besides an increased relative risk support the concept that DCIS is pre-malignant: 1) When breast cancer occurs in these patients it regularly occurs in the same region of the same breast where the DCIS was found; and 2) DCIS is frequently present in tissue adjacent to invasive breast cancer (Ottesen et al, 1992; Schwartz et al, 1992). For these reasons DCIS very likely represents a rate-limiting step in the development of invasive breast cancer in women.

DCIS (sometimes called intraductal carcinoma) is a group of lesions in which the cells have grown to completely fill the duct with patterns similar to invasive cancer, but do not invade outside the duct or show metastases at presentation. DCIS occurs in two forms: comedo DCIS and non-comedo DCIS. Comedo DCIS is often a grossly palpable lesion which was probably considered "cancer" in the 19th and early 20th century and progresses to cancer (without definitive therapy) in at least 50% of patients within three years (Ottesen et al, 1992; Page et al, 1982). Most of the molecular alterations which have been reported in pre-malignant breast disease have been observed in cases of comedo DCIS (Poller et al, 1993; Radford et al, 1993; and, Tsuda et al, 1993). Non-comedo DCIS is detected by microscopic analysis of breast aspirates or biopsies and is associated with a 10 fold increased risk of breast cancer, which corresponds to a 25–30% absolute risk of breast cancer within 15 years (Ottesen et al, 1992; Page et al, 1982; and, Ward et al, 1992).

Widespread application of mammography has changed the relative incidence of comedo and non-comedo DCIS such that NCDCIS now represents the predominant form of DCIS diagnosed in the United States (Ottesen et al, 1992; Page et al, 1982; and Pierce et al, 1992). Both forms of DCIS generally recur as invasive cancer at the same site as the pre-malignant lesion (without definitive therapy). The precursor lesions to DCIS are probably atypical ductal hyperplasia and proliferative disease without atypia which are associated with lower rates of breast cancer development, but show further increased risk when associated with a family history of breast cancer (Dupont et al, 1985; Dupont et al, 1989; Dupont et al, 1993; Lawrence, 1990; London et al, 1991; Page et al, 1982; Page et al, 1985; Page et al, 1991; Page et al, 1978; Simpson et al, 1992; Solin et al, 1991; Swain, 1992; Weed et al, 1990).

What is needed, then, is a sensitive method of detection and diagnosis of breast cancer when the cancerous cells are still in the pre-invasive stage. To illustrate the usefulness in early breast cancer detection of a marker gene and its encoded protein, consider the dramatic impact that prostate specific antigen has had on early stage prostate cancer. This method of early detection and diagnosis of breast cancer is presently lacking in the prior art.

Breast cancer occurs in hereditary and sporadic forms. Recently the BRCA1 gene has been cloned and shown to be mutated in kindreds with hereditary breast and ovarian cancer (Hall et al. 1990, Miki, Y. et al. 1994, Friedman et al. 1994, Castilla et al. 1994, Simard et al. 1994). Although 92% of families with two or more cases of early-onset breast cancer and two cases of ovarian cancer have germ-line mutations in BRCA1 (Narod et al. in press), the gene has not been shown to be mutated in any truly sporadic case to date (Futreal et al. 1994). Despite the surprising paucity of somatically acquired mutations in sporadic breast cancer, it is still a likely tumor suppressor gene with a key role in breast epithelial cell biology. The BRCA1 gene encodes a protein of 1863 amino acids with a predicted zinc finger domain observed in proteins which regulate gene transcription. Until the discovery of the function of the BRCA1 gene in conjuction with the development of the present invention, the function was unknown.

SUMMARY OF THE INVENTION

Epidemiologic studies have established that NCDCIS of the breast is associated with a ten-fold increased risk of breast cancer (absolute risk of 25–30%). It seems likely that this pre-invasive lesion is a determinate precursor of breast cancer because the subsequent development of breast cancer is regularly in the same region of the same breast in which the NCDCIS lesion was found. Important aspects of the present invention concern isolated DNA segments and those isolated DNA segments inserted into recombinant vectors encoding differentially expressed marker genes in abnormal tissue, specifically in NCDCIS, as compared with those expressed in normal tissue, and the creation and use of recombinant host cells through the application of DNA technology, which express these differentially expressed marker genes (Sambrook et al, 1989).

Because there are no cell lines or animal models which clearly display known characteristics of pre-invasive breast disease, human breast tissue samples are essential for studying pre-invasive breast disease. Using human tissue samples, we subsequently have developed a method for cDNA cloning from histologically identified lesions in human breast biopsies. We have used this method to clone genes which are differentially expressed in pre-invasive breast lesions such as NCDCIS lesions as compared to genes expressed in normal tissue. The differentially expressed genes detected in pre-invasive breast cancer are called marker genes. Identification of marker genes for pre-invasive breast disease provides improved methods for detection and diagnosis of pre-invasive breast cancer tissue, and further provides marker genes for studies of the molecular events involved in progression from pre-invasive to malignant breast disease.

Analysis of marker gene expression in NCDCIS presents the advantage that cancerous breast tissue at that stage is non-invasive. Detection and diagnosis of NCDCIS by means of differentially expressed marker genes compared to the same marker genes in normal breast tissue, would allow a greater ability to detect, prevent and treat the disease before it becomes invasive and metastasizes. The stage or intermediate condition of NCDCIS is a particularly good candidate for early intervention because it is 1) prior to any invasion and thus prior to any threat to life; 2) it is followed by invasive carcinoma in over 30% of cases if only treated by biopsy; and, 3) there is a long "window" of opportunity (4–8 years) approximately before invasive neoplasia occurs. Thus, NCDCIS is an ideal target for early diagnosis. While these morphologically defined intermediate endpoints have been widely accepted, progress in defining the molecular correlates of these lesions has been hampered by an inability to identify and sample them in a manner which would allow the application of molecular techniques.

Frozen tissue blocks from breast biopsies were used to construct and screen cDNA libraries prepared from NCDCIS tissue, normal breast tissue, breast cancer tissue, and normal human breast epithelial cells. Several cDNAs which were differentially expressed in human DCIS epithelial cells compared to normal breast epithelial cells were cloned and sequenced. One gene which is differentially expressed is the M2 subunit of RibRed which is expressed at low levels in human breast epithelial cells but at higher levels in 4 out of 5 DCIS tissue samples. It is presumed that the altered morphologic appearance and determinant biologic behavior of DCIS results from altered expression of genes (such as RibRed) which is important in the induction of breast cancer in humans.

This invention, therefore, provides a method of detecting and diagnosing pre-invasive breast cancer by analyzing marker genes which are differentially expressed in non-comedo DCIS cells. Histopathologic studies have demonstrated that these morphologic patterns in breast tissue lead to invasive breast cancer in at least 20–30% of patients. The present method analyzes gene expression in normal, pre-malignant and malignant breast biopsies; and, it allows simultaneous comparison and cloning of marker genes which are differentially expressed in pre-invasive breast cancer. These marker genes can then be used as probes to develop other diagnostic tests for the early detection of pre-invasive breast cancer.

The present invention concerns DNA segments, isolatable from both normal and abnormal human breast tissue, which are free from total genomic DNA. The isolated DCIS-1 protein product is the regulatory element of the RibRed enzyme. This and all other isolatable DNA segments which are differentially expressed in preinvasive breast cancer can be used in the detection, diagnosis and treatment of breast cancer in its earliest and most easily treatable stages. As used herein, the term "abnormal tissue" refers to pre-invasive and invasive breast cancer tissue, as exemplified by collected samples of non-comedo or comedo DCIS tissues.

As used herein, the term "DNA segment" refers to a DNA molecule which has been isolated free of total genomic DNA of a particular species. Therefore, a DNA segment encoding a differentially expressed protein (as measured by the expression of mRNA) in abnormal tissue refers to a DNA segment which contains differentially expressed-coding sequences in abnormal tissue as compared to those expressed in normal tissue, yet is isolated away from, or purified free from, total genomic DNA of Homo sapiens sapiens. Furthermore, a DNA segment encoding a BRCA1 protein refers to a DNA segment which contains BRCA1 coding sequences, yet is isolated away from, or purified free from, total genomic DNA of Homo sapiens sapiens. Included within the term "DNA segment", are DNA segments and smaller fragments of such segments, and also recombinant vectors, including, for example, plasmids, cosmids, phage, viruses, and the like.

Similarly, a DNA segment comprising an isolated or purified differentially expressed gene or comprising an isolated or purified BRCA1 gene refers to a DNA segment including differentially expressed coding sequences or BRCA1 coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences and cDNA sequences. "Isolated substantially away from other coding sequences" means that the gene of interest, in this case, any differentially expressed marker gene or the BRCA1 gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode differentially expressed genes in pre-invasive breast cancer, each which includes within its amino acid sequence an amino acid sequence in accordance with SEQ ID NO:1, SEQ ID NO:2, SEQ ID NO:3, SEQ ID NO:4, SEQ ID NO:5, SEQ ID NO:6, or SEQ ID NO:7, all seq id no:s 1–7 are derived from non-comedo DCIS samples from Homo sapiens sapiens. In other particular embodiments, the invention concerns isolated DNA segments and recombinant vectors incorporating DNA sequences which encode the M2 subunit of human RibRed that includes within its amino acid sequence the similar amino acid sequence of hamster RibRed corresponding to the M2 subunit of hamster RibRed.

In certain embodiments, the invention concerns isolated DNA segments and recombinant vectors which partially or wholly encode a protein or peptide that includes within its amino acid sequence an amino acid sequence essentially as partially or wholly encoded, respectively, by SEQ ID NO:1, SEQ ID NO:2, SEQ ID NO:3, SEQ ID NO:4, SEQ ID NO:5, SEQ ID NO:6, or SEQ ID NO:7. Naturally, where the DNA segment or vector encodes a full length differentially expressed protein, or is intended for use in expressing the differentially expressed protein, the most preferred sequences are those which are essentially as set forth in SEQ ID NO:1, SEQ ID NO:2, SEQ ID NO:3, SEQ ID NO:4, SEQ ID NO:5, SEQ ID NO:6, or SEQ ID NO:7 and which encode a protein that exhibits differential expression, e.g., as may be determined by the differential display or differential sequencing assay, as disclosed herein.

The term "a sequence essentially as set forth in SEQ ID NO:1, SEQ ID NO:2, SEQ ID NO:3, SEQ ID NO:4, SEQ ID NO:5, SEQ ID NO:6, or SEQ ID NO:7" means that the sequence substantially corresponds to a portion of SEQ ID NO:1, SEQ ID NO:2, SEQ ID NO:3, SEQ ID NO:4, SEQ ID NO:5, SEQ ID NO:6, or SEQ ID NO:7, respectively, and has relatively few nucleotides which are not identical to, or a biologically functional equivalent of, the nucleotides of the respective SEQ ID NO:1, SEQ ID NO:2, SEQ ID NO:3, SEQ ID NO:4, SEQ ID NO:5, SEQ ID NO:6, or SEQ ID NO:7. The term "biologically functional equivalent" is well understood in the art and is further defined in detail herein, for example see pages 24 through 25. Accordingly, sequences which have between about 70% and about 80%; or more preferably, between about 81% and about 90%; or even more preferably, between about 91% and about 99%; of amino acids which are identical or functionally equivalent to the amino acids of SEQ ID NO:1, SEQ ID NO:2, SEQ ID NO:3, SEQ ID NO:4, SEQ ID NO:5, SEQ ID NO:6, or SEQ ID NO:7 will be sequences which are "essentially as set forth in SEQ ID NO:1, SEQ ID NO:2, SEQ ID NO:3, SEQ ID NO:4, SEQ ID NO:5, SEQ ID NO:6, or SEQ ID NO:7", respectively.

In particular embodiments, the invention concerns a drug screening method and a gene therapy method that use isolated DNA segments and recombinant vectors incorporating DNA sequences which encode a protein that includes within its amino acid sequence an amino acid sequence in accordance with SEQ ID NO:49, SEQ ID NO:49 derived from breast tissue from Homo sapiens. In other particular embodiments, the invention concerns isolated DNA sequences and recombinant DNA vectors incorporating DNA sequences which encode a protein that includes with its amino acid sequence the amino acid sequence of the BRCA1 gene product from human breast tissue.

In certain embodiments, the invention concerns methods using isolated DNA segments and recombinant vectors which partially or wholly encode a protein or peptide that includes within its amino acid sequence an amino acid sequence essentially as set forth in SEQ ID NO:49. Naturally, where the DNA segment or vector encodes a full length BRCA1 protein, or is intended for use in expressing the BRCA1 protein, the most preferred sequences are those which are essentially as set forth in SEQ ID NO:47 and which encode a protein that retains activity as a negative growth regulator in human breast cells, as may be determined by antisense assay, as disclosed herein.

The term "a sequence essentially as set forth in SEQ ID NO:1, SEQ ID NO:2, SEQ ID NO:3, SEQ ID NO:4, SEQ ID NO:5, SEQ ID NO:6, or SEQ ID NO:7" means that the sequence substantially corresponds to a portion of SEQ ID NO:1, SEQ ID NO:2, SEQ ID NO:3, SEQ ID NO:4, SEQ ID NO:5, SEQ ID NO:6, or SEQ ID NO:7, respectively, and has relatively few nucleotides which are not identical to, or a biologically functional equivalent of, the nucleotides of the respective SEQ ID NO:1, SEQ ID NO:2, SEQ ID NO:3, SEQ ID NO:4, SEQ ID NO:5, SEQ ID NO:6, or SEQ ID NO:7. The term "biologically functional equivalent" is well understood in the art and is further defined in detail herein, for example see pages 24 through 25. Accordingly, sequences which have between about 70% and about 80%; or more preferably, between about 81% and about 90%; or even more preferably, between about 91% and about 99%; of amino acids which are identical or functionally equivalent to the amino acids of SEQ ID NO:1, SEQ ID NO:2, SEQ ID NO:3, SEQ ID NO:4, SEQ ID NO:5, SEQ ID NO:6, or SEQ ID NO:7 will be sequences which are "essentially as set forth in SEQ ID NO:1, SEQ ID NO:2, SEQ ID NO:3, SEQ ID NO:4, SEQ ID NO:5, SEQ ID NO:6, or SEQ ID NO:7", respectively.

The term "a sequence essentially as set forth in SEQ ID NO:49" means that the sequence substantially corresponds to a portion of SEQ ID NO:49 and has relatively few amino acids which are not identical to, or a biologically functional equivalent of, the nucleotides of SEQ ID NO:49. The term "biologically functional equivalent" is well understood in the art and is further defined in detail herein, for example see pages 24 through 25. Accordingly, sequences which have between about 70% and about 80%; or more preferably, between about 81% and about 90%; or even more preferably, between about 91% and about 99%; of amino acids which are identical or functionally equivalent to the amino acids of SEQ ID NO:49 will be sequences which are "essentially as set forth in SEQ ID NO:49".

In certain other embodiments, the invention concerns isolated DNA segments and recombinant vectors that include within their sequence a nucleic acid sequence essentially as set forth in SEQ ID NO:1, SEQ ID NO:2, SEQ ID NO:3, SEQ ID NO:4, SEQ ID NO:5, SEQ ID NO:6, and SEQ ID NO:7. The term "essentially as set forth in SEQ ID NO:1, SEQ ID NO:2, SEQ ID NO:3, SEQ ID NO:4, SEQ ID NO:5, SEQ ID NO:6, and SEQ ID NO:7" is used in the same sense as described above and means that the nucleic acid sequence substantially corresponds to a portion of SEQ ID NO:1, SEQ ID NO:2, SEQ ID NO:3, SEQ ID NO:4, SEQ ID NO:5, SEQ ID NO:6, and SEQ ID NO:7, respectively, and has relatively few codons which are not identical, or functionally equivalent, to the codons of SEQ ID NO:1, SEQ ID NO:2, SEQ ID NO:3, SEQ ID NO:4, SEQ ID NO:5, SEQ ID NO:6, and SEQ ID NO:7, respectively. Again, DNA segments which encode proteins exhibiting differential expression will be most preferred. The term "functionally equivalent codon" is used herein to refer to codons that encode the same amino acid, such as the six codons for arginine or serine, and also refers to codons that encode biologically equivalent amino acids (see FIG. 8).

In certain other embodiments, the invention concerns a method for screening drugs and a gene therapy method which involve the use of isolated DNA segments and recombinant vectors that include within their sequence a nucleic acid sequence essentially as set forth in SEQ ID NO:47 and SEQ ID NO:48. The term "essentially as set forth in SEQ ID NO:47 and SEQ ID NO:48" is used in the same sense as described above and means that the nucleic acid sequence substantially corresponds to a portion of SEQ ID NO:47 and SEQ ID NO:48 respectively, and has relatively few codons which are not identical, or functionally equivalent, to the codons of SEQ ID NO:47 and SEQ ID NO:48, respectively. Again, DNA segments which encode proteins exhibiting the negative regulatory activity of the BRCA1 will be most preferred. The term "functionally equivalent codon" is used herein to refer to codons that encode the same amino acid, such as the six codons for arginine or serine, and also refers to codons that encode biologically equivalent amino acids (see FIG. 8).

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences which have between about 20% and about 50%; or more preferably, between about 50% and about 70%; or even more preferably, between about 70% and about 99%; of nucleotides which are identical to the nucleotides of SEQ ID NO:1, SEQ ID NO:2, SEQ ID NO:3, SEQ ID NO:4, SEQ ID NO:5, SEQ ID NO:6, and SEQ ID NO:7 will be sequences which are "essentially as set forth in SEQ ID NO:1, SEQ ID NO:2, SEQ ID NO:3, SEQ ID NO:4, SEQ ID NO:5, SEQ ID NO:6, and SEQ ID NO:7", respectively. Sequences which are essentially the same as those set forth in SEQ ID NO:1, SEQ ID NO:2, SEQ ID NO:3, SEQ ID NO:4, SEQ ID NO:5, SEQ ID NO:6, and SEQ ID NO:7 may also be functionally defined as sequences which are capable of hybridizing to a nucleic acid segment containing the complement of SEQ ID NO:1, SEQ ID NO:2, SEQ ID NO:3, SEQ ID NO:4, SEQ ID NO:5, SEQ ID NO:6, and SEQ ID NO:7, respectively, under relatively stringent conditions. Suitable relatively stringent hybridization conditions will be well known to those of skill in the art (Sambrook et al, 1989).

Excepting intronic or flanking regions, and allowing for the degeneracy of the genetic code, sequences which have between about 20% and about 50%; or more preferably, between about 50% and about 70%; or even more preferably, between about 70% and about 99%; of nucleotides which are identical to the nucleotides of SEQ ID NO:47 and SEQ ID NO:48 will be sequences which are "essentially as set forth in SEQ ID NO:47 and SEQ ID NO:48", respectively. Sequences which are essentially the same as those set forth in SEQ ID NO:47 and SEQ ID NO:48 may also be functionally defined as sequences which are capable of hybridizing to a nucleic acid segment containing the complement of SEQ ID NO:47 and SEQ ID NO:48, respectively, under relatively stringent conditions. Suitable relatively stringent hybridization conditions will be well known to those of sill in the art (Sambrook et al, 1989).

It is also important to understand the molecular events which lead to progression from pre-invasive to invasive breast cancer. Breast cancer is a disease that is presumed to involve a series of genetic alterations that confer increasing growth independence and metastatic capability on somatic cells. Identifying the molecular events that lead to the initial development of a neoplasm is therefore critical to understanding the fundamental mechanisms by which tumors arise and to the selection of optimal targets for gene therapy and chemopreventive agents. As intermediate endpoints in neoplastic development, some pre-malignant breast lesions represent important, and possibly rate-limiting steps in the progression of human breast cancer, and careful epidemiological studies have established the relative risk for breast cancer development for specific histologic lesions. In particular, invasive breast cancer develops in the region of the previous biopsy site in at least 25–30% of patients following diagnosis of non-comedo DCIS providing strong evidence that this pre-malignant lesion is a determinant event in breast cancer progression. While these morphologically defined intermediate endpoints have been widely accepted, progress in defining the molecular correlates of these lesions has been hampered by an inability to identify and sample them in a manner which would allow the application of molecular techniques.

The present invention includes a comparison of gene expression between multiple breast tissue biopsy samples as a means to identify differentially expressed genes in premalignant breast disease compared with normal breast tissue. These genetic markers should be extremely useful reagents for early diagnosis of breast cancer, and for the delineation of molecular events in progression of breast cancer.

Identification of gene markers which are expressed in the majority of pre-invasive breast cancer tissue samples involves cDNA library preparation from both normal and abnormal tissue. This is followed by either a modified differential display method or a differential screening method to identify differential expression of genes which is subsequently confirmed by RT-PCR, nuclease protection assays and in situ hybridization of DCIS tissue RNA and control tissue RNAs (Sambrook et al, 1989). Use of genetic engineering methods can bias the screening to specifically identify genes whose encoded proteins are secreted or are present at the cell surface, in order to find proteins which will be useful markers for diagnostic blood tests (secreted proteins) or for diagnostic imaging studies (cell surface proteins).

Thus, the method of the present invention begins with the collection of at least one tissue sample by a microscopically-directed collection step in which a punch biopsy is obtained exclusively from abnormal tissue which exhibits histological or cytological characteristics of pre-invasive breast cancer. Preferably, the sample site will be an isolatable tissue structure, such as ductal epithelial cells from pre-invasive breast cancer tissue. The mRNA is purified from the sample. Then, a cDNA library is prepared from the mRNA purified from the abnormal tissue sample (Sambrook et al, 1989).

A normal tissue sample is then obtained from the patient, using a sample site from an area of tissue which does not exhibit histological or cytological characteristics of pre-invasive cancer. A cDNA library is also prepared from this normal tissue sample.

The abnormal tissue cDNA library can then be compared with the normal tissue cDNA library by differential display or differential screening to determine whether the expression of at least one marker gene in the abnormal tissue sample is different from the expression of the same marker gene in the normal tissue sample.

Further diagnostic steps can be added to the method by cloning the marker gene using sequence-based amplification to create a cloned marker gene which can then be DNA-sequenced in order to derive the protein sequence. The protein sequence is then used to generate antibodies which will recognize these proteins by antibody recognition of the antigen. The presence of the antibody-recognized antigen can then be detected by means of conventional medical diagnostic tests.

This invention also includes methods of screening for compounds and gene therapy methods using the BRCA1 gene. BRCA1 mRNA is expressed at 5–10 fold higher levels in normal mammary tissue than in invasive breast cancer samples. Having demonstrated that mRNA expression levels of BRCA1 are higher in normal mammary cells than in cancer cells, antisense methods were used to test the hypothesis that BRCA1 expression inhibits cell growth. These tests showed that diminished expression of BRCA1 increased the proliferative rate of breast cells.

An object of the present invention, then, is to provide a method of early detection of pre-invasive breast cancer in human tissue.

It is a further object of this invention to identify early marker genes for pre-invasive breast disease which can be used in screening methods for early pre-invasive breast cancer.

It is also an object of this invention to produce a cDNA library from pre-invasive breast cancer tissue resulting in a permanent genetic sample of that pre-invasive breast cancer tissue.

It is also an object of this invention to provide a drug or biological screening method using the BRCA 1 promoter region and gene therapy method using the BRCA 1 gene.

| List of Abbreviations | |
|---|---|
| TPA | Phorbol 12-myristate 13-acetate |
| MCF-7 | An immortalized cell line derived from a metastasis of human breast cancer |
| HMEC | A primary (non-immortalized) cell line derived from breast epithelial cells obtained during reduction mammoplasty |
| DCIS | Ductal Carcinoma-in-situ |
| NCDC | Non-Comedo Ductal Carcinoma in situ |
| cDNA | Complementary DNA obtained from an RNA template |
| DNA | Deoxyribonucleic Acid |
| RT-PCR | Reverse Transcriptase-Polymerase Chain Reaction |
| RibRed | Ribonucleotide Reductase |

BRIEF DESCRIPTION OF THE FIGURES

FIG. 1 shows Table I which describes anatomic lesion types in the human breast with pre-malignant implication.

FIG. 6 shows a comparison of the sequence between DCIS-1 (SEQ ID NO:1) and the human (SEQ ID NOs: 56–57) and hamster (SEQ ID NOs: 58–61) genes.

FIG. 8 is Table ii which displays the genetic code.

FIG. 9 is a Table which lists differentially expressed marker genes from pre-invasive human breast tissue.

DESCRIPTION OF THE PREFERRED EMBODIMENT

Figure 2:
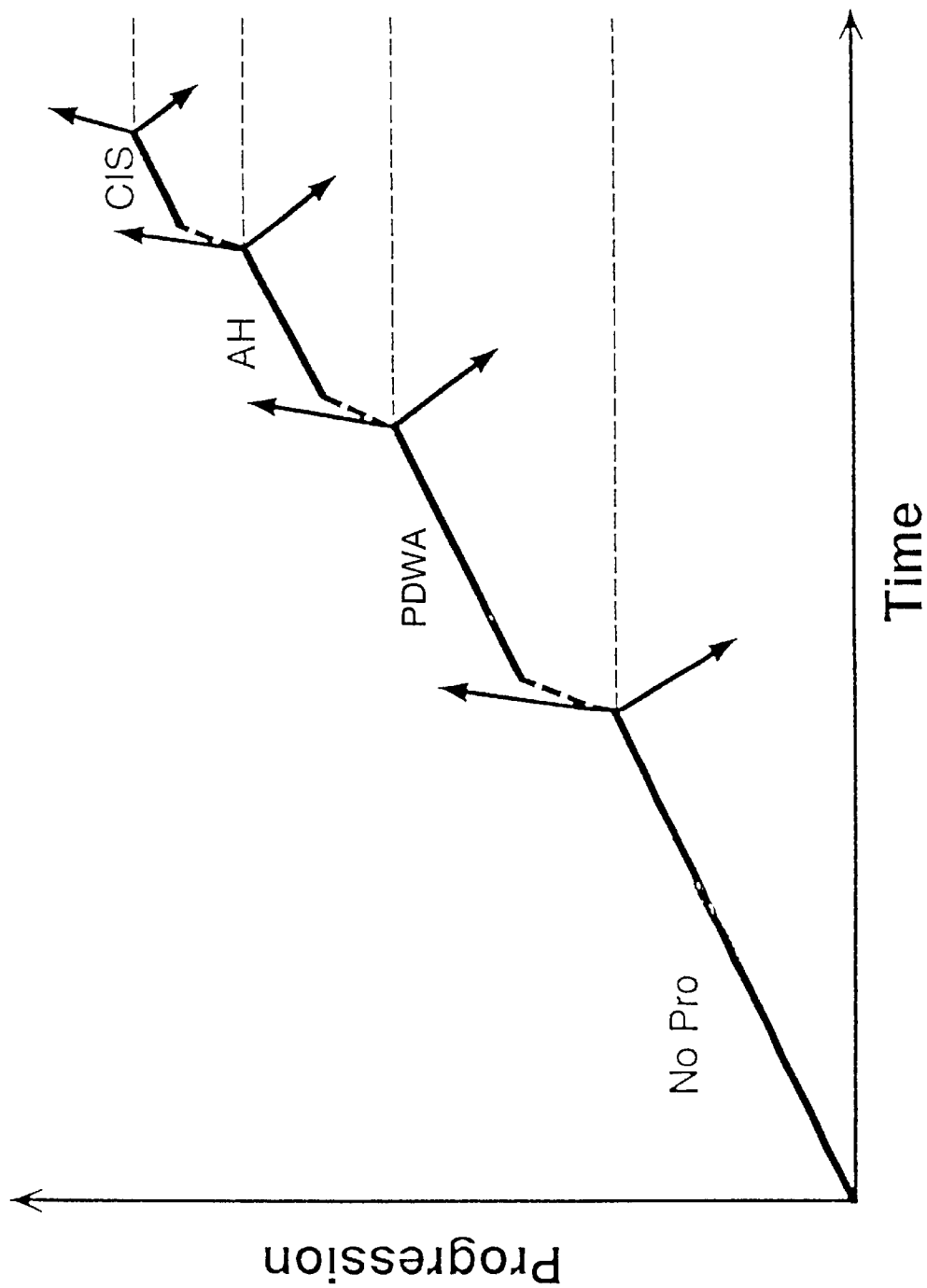
FIG. 2 shows a model for pre-malignant conditions, highlighting magnitude of risk for progression to clinical malignancy. Terms from human breast neoplasia are used: No Pro=no proliferative disease; PDWA=proliferative disease without alypia; AH=typical hyperplasia; and CIS=carcinoma in situ. As is the proposal of tumor progression, each stage is more likely to proceed to the next (dotted lines), but could also remain stable (horizontal lines, probably fairly frequent), or directly proceeds to development of a clone of cells with malignant behavior (vertical lines, becoming more likely further to the right.

For the purposes of the subsequent description, the following definitions will be used:

Nucleic acid sequences which are "complementary" are those which are capable of base-pairing according to the standard Watson-Crick complementarity rules. That is, that the larger purines will always base pair with the smaller pyrimidines to form only combinations of Guanine paired with Cytosine (G:C) and Adenine paired with either Thymine (A:T) in the case of DNA or Adenine paired with Uracil (A:U) in the case of RNA.

"Hybridization techniques" refer to molecular biological techniques which involve the binding or hybridization of a probe to complementary sequences in a polynucleotide. Included among these techniques are northern blot analysis, southern blot analysis, nuclease protection assay, etc.

"Hybridization" and "binding" in the context of probes and denatured DNA are used interchangeably. Probes which are hybridized or bound to denatured DNA are aggregated to complementary sequences in the polynucleotide. Whether or not a particular probe remains aggregated with the polynucleotide depends on the degree of complementarity, the length of the probe, and the stringency of the binding conditions. The higher the stringency, the higher must be the degree of complementarity and/or the longer the probe.

"Probe" refers to an oligonucleotide or short fragment of DNA designed to be sufficiently complementary to a sequence in a denatured nucleic acid to be probed and to be bound under selected stringency conditions.

"Label" refers to a modification to the probe nucleic acid that enables the experimenter to identify the labeled nucleic acid in the presence of unlabeled nucleic acid. Most commonly, this is the replacement of one or more atoms with radioactive isotopes. However, other labels include covalently attached chromophores, fluorescent moeities, enzymes, antigens, groups with specific reactivity, chemiluminescent moeities, and electrochemically detectable moeities, etc.

"Marker gene" refers to any gene selected for detection which displays differential expression in abnormal tissue as opposed to normal tissue. It is also referred to as a differentially expressed gene.

"Marker protein" refers to any protein encoded by a "marker gene" which protein displays differential expression in abnormal tissue as opposed to normal tissue.

"Tissuemizer" describes a tissue homogenization probe.

"Abnormal tissue" refers to pathologic tissue which displays cytologic, histologic and other defining and derivative features which differ from that of normal tissue. This includes in the case of abnormal breast tissue, among others, pre-invasive and invasive neoplasms.

"Normal tissue" refers to tissue which does not display any pathologic traits.

"PCR technique" describes a method of gene amplification which involves sequenced-based hybridization of primers to specific genes within a DNA sample (or library) and subsequent amplification involving multiple rounds of annealing, elongation and denaturation using a heat-stable DNA polymerase.

"RT-PCR" is an abbreviation for reverse transcriptase-polymerase chain reaction. Subjecting mRNA to the reverse transcriptase enzyme results in the production of cDNA which is complementary to the base sequences of the mRNA. Large amounts of selected cDNA can then be produced by means of the polymerase chain reaction which relies on the action of heat-stable DNA polymerase produced by *Thermus aquaticus* for its amplification action.

"Microscopically-directed" refers to the method of tissue sampling by which the tissue sampled is viewed under a microscope during the sampling of that tissue such that the sampling is precisely limited to a given tissue type, as the investigator requires. Specifically, it is a collection step which involves the use of a punch biopsy instrument. This surgical instrument is stereotactically manually-directed to harvest exclusively from abnormal tissue which exhibits histologic or cytologic characteristics of pre-invasive cancer. The harvest is correlated with a companion slide, stained to recognize the target tissue.

"Differential display" describes a method in which expressed genes are compared between samples using low stringency PCR with random oligonucleotide primers.

"Differential screening" describes a method in which genes within cDNA libraries are compared between two samples by differential hybridization of cDNAs to probes prepared from each library.

"Nuclease protection assay" refers to a method of RNA quantitation which employs strand specific nucleases to identify specific RNAs by detection of duplexes.

"Differential expression" describes the phenomenon of differential genetic expression seen in abnormal tissue in comparison to that seen in normal tissue.

"Isolatable tissue structure" refers to a tissue structure which when visualized microscopically or otherwise is able to be isolated from other different surrounding tissue types.

"In situ hybridization of RNA" refers to the use of labeled DNA probes employed in conjunction with histological sections on which RNA is present and with which the labeled probe can hybridize allowing an investigator to visualize the location of the specific RNA within the cell.

"Comedo DCIS cells" refers to cells comprising an in situ lesion with the combined features of highest grade DCIS.

"Non-comedo DCIS cells" refers to cells of DCIS lesions without comedo features.

"Cloning" describes separation and isolation of single genes.

"Sequencing" describes the determination of the specific order of nucleic acids in a gene or polynucleotide.

The present invention provides a method for detecting and diagnosing cancer by analyzing marker genes which are differentially expressed in early, pre-invasive breast cancer, specifically in non-comedo DCIS cells. Our histopathologic studies have demonstrated that certain morphologic patterns in breast tissue are pre-malignant, leading to invasive breast cancer in at least 20–30% of patients. We have developed a new method for analyzing gene expression in normal, pre-malignant and malignant breast biopsies which allows simultaneous comparison and cloning of marker genes which are differentially expressed in pre-invasive breast cancer. These marker genes (which appear as differentially expressed genes in pre-invasive breast cancer) can be used as probes to develop diagnostic tests for the early detection of pre-invasive breast cancer (Sambrook, 1989).

The present invention thus comprises a method of identification of marker genes which are expressed in the majority of pre-invasive breast cancer tissue samples. It involves cDNA library preparation followed by a modified differential display method. Use of genetic engineering methods (Sambrook, 1989) can bias the screening to specifically identify genes whose encoded proteins are secreted or are present at the cell surface, in order to find proteins which will be useful markers for diagnostic blood tests (secreted proteins) or for diagnostic imaging studies (cell surface proteins).

Naturally, the present invention also encompasses DNA segments which are complementary, or essentially complementary, to the sequence set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:47 and SEQ ID NO:48. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:1, SEQ ID NO:2, SEQ ID NO:3, SEQ ID NO:4, SEQ ID NO:5, SEQ ID NO:6, SEQ ID NO:7, SEQ ID NO:47 and SEQ ID NO:48 under relatively stringent conditions such as those described herein.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:1, SEQ ID NO:2, SEQ ID NO:3, SEQ ID NO:4, SEQ ID NO:5, SEQ ID NO:6, SEQ ID NO:7, SEQ ID NO:47 and SEQ ID NO:48, such as about 10 nucleotides, and which are up to 10,000 or 5,000 base pairs in length, with segments of 500 being preferred in most cases. DNA segments with total lengths of about 1,000, 500, 200, 100 and about 50 base pairs in length are also contemplated to be useful.

It will also be understood that this invention is not limited to the particular nucleic acid and amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:47, SEQ ID NO:48, and SEQ ID NO:49. Recombinant vectors and isolated DNA segments may therefore variously include the differentially expressed coding regions or the BRCA1 coding regions themselves, coding regions bearing selected alterations or modifications in the basic coding region, or they may encode larger polypeptides which nevertheless include differentially expressed-coding regions and the BRCA1 coding regions or may encode biologically functional equivalent proteins or peptides which have variant amino acids sequences.

The DNA segments of the present invention encompass biologically functional equivalent differentially expressed proteins and peptides biologically functional equivalent proteins of BRCA1. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test site-directed mutants or others in order to examine carcinogenic activity of the differentially expressed marker genes at the molecular level.

If desired, one may also prepare fusion proteins and peptides, e.g., where the differentially expressed marker gene coding regions are aligned within the same expression unit with other proteins or peptides having desired functions, such as for purification or immunodetection purposes (e.g., proteins which may be purified by affinity chromatography and enzyme label coding regions, respectively).

Recombinant vectors form important further aspects of the present invention. Particularly useful vectors are contemplated to be those vectors in which the coding portion of the DNA segment is positioned under the control of a promoter. The promoter may be in the form of the promoter which is naturally associated with a RIBRED gene, e.g., in human cells, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a differentially expressed marker gene or the BRCA1 gene in its natural environment. Such promoters may include MMTV promoters normally associated with other genes, and/or promoters isolated from any other bacterial, viral, eukaryotic, or mammalian cell. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al. (1989). The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to appropriate bacterial promoters.

As mentioned above, in connection with expression embodiments to prepare recombinant differentially expressed marker gene encoded proteins and peptides, it is contemplated that longer DNA segments will most often be used, with DNA segments encoding the entire differentially expressed protein or subunit being most preferred. However, it will be appreciated that the use of shorter DNA segments to direct the expression of differentially expressed peptides or epitopic core regions, such as may be used to generate anti-marker protein antibodies, also falls within the scope of the invention (Harlow et al, 1988).

DNA segments which encode peptide antigens from about 15 to about 50 amino acids in length, or more preferably, from about 15 to about 30 amino acids in length are contemplated to be particularly useful. The C terminus of proteins provide an excellent region for peptide antigen recognition (Harlow et al, 1988). DNA segments encoding peptides will generally have a minimum coding length in the order of about 45 to about 147, or to about 90 nucleotides. DNA segments encoding partial length peptides may have a minimum coding length in the order of about 50 nucleotides for a polypeptide in accordance with seq id no:3, or about 264 nucleotides for a polypeptide in accordance with SEQ ID NO:1.

In addition to their use in directing the expression of the differentially expressed marker proteins, the nucleic acid sequences disclosed herein also have a variety of other uses. For example, they also have utility as probes or primers in nucleic acid hybridization embodiments. As such, it is contemplated that oligonucleotide fragments corresponding to the sequences of SEQ ID NO:1, SEQ ID NO:2, SEQ ID NO:3, SEQ ID NO:4, SEQ ID NO:5, SEQ ID NO:6, and SEQ ID NO:7 for stretches of between about 10 to 15 nucleotides and about 20 to 30 nucleotides will find particular utility. Longer complementary sequences, e.g., those of about 40, 50, 100, 200, 500, 1000, and even up to full length sequences of about 2,000 nucleotides in length, will also be of use in certain embodiments.

The ability of such nucleic acid probes to specifically hybridize to differentially expressed marker gene sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having stretches of 20, 30, 50, or even of 500 nucleotides or so, complementary to SEQ ID NO:1, SEQ ID NO:2, SEQ ID NO:3, SEQ ID NO:4, SEQ ID NO:5, SEQ ID NO:6, and SEQ ID NO:7 are particularly contemplated as hybridization probes for use in, e.g., Southern and Northern blotting. This would allow differentially expressed structural or regulatory genes to be analyzed, both in patients and sample tissue from pre-invasive and invasive breast tissue. The total size of fragment, as well as the size of the complementary stretch(es), will ultimately depend on the intended use or application of the particular nucleic acid segment. Smaller fragments will generally find use in hybridization embodiments, wherein the length of the complementary region may be varied, such as between about 10 and about 100 nucleotides, but larger complementary stretches of up to about 300 nucleotides may be used, according to the length complementary sequences one wishes to detect.

Nucleic Acid Hybridization

The use of a hybridization probe of about 10 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired.

Hybridization probes may be selected from any portion of any of the sequences disclosed herein. All that is required is to review the sequences set forth in SEQ ID NO:1, SEQ ID NO:2, SEQ ID NO:3, SEQ ID NO:4, SEQ ID NO:5, SEQ ID NO:6, and SEQ ID NO:7 and to select any continuous portion of one of the sequences, from about 10 nucleotides in length up to and including the full length sequence, that one wishes to utilise as a probe or primer. The choice of probe and primer sequences may be governed by various factors, such as, by way of example only, one may wish to employ primers from towards the termini of the total sequence, or from the ends of the functional domain-encoding sequences, in order to amplify further DNA; one may employ probes corresponding to the entire DNA, or to the 5' region, to clone marker-type genes from other species or to clone further marker-like or homologous genes from any species including human; and one may employ randomly selected, wild-type and mutant probes or primers with sequences centered around the RibRed M2 subunit encoding sequence to screen DNA samples for differentially expressed levels of RibRed, such as to identify human subjects which may be expressing differential levels of RibRed and thus may be susceptible to breast cancer.

The process of selecting and preparing a nucleic acid segment which includes a sequence from within SEQ ID NO:1, SEQ ID NO:2, SEQ ID NO:3, SEQ ID NO:4, SEQ ID NO:5, SEQ ID NO:6, and SEQ ID NO:7 may alternatively be described as "preparing a nucleic acid fragment". Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR technology of U.S. Pat. No. 4,603,102 (incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of differentially expressed marker genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating specific differentially expressed marker genes.

Of course, for some applications, for example, where one desires to prepare mutants employing a mutant primer strand hybridized to an underlying template or where one seeks to isolate marker gene sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label. (Sambrook et al, 1989).

In a preferred embodiment of the method, certain preliminary procedures are necessary to prepare the sample tissue and the probes before the detection of differential expression of marker genes in abnormal tissue as compared to that in normal tissue can be accomplished.

Sample Preparation

RNA Purification

RNA was isolated from frozen tissue samples by mincing of microdisected frozen tissue fragments with a razor blade and then adding 800 microliter of 5.6M guanidinium to increase mixing, followed by a 30 second microcentrifuge centrifugation at 14,000 rpm to remove particulate matter. The supernatant was then removed and the viscosity was reduced by multiple aspirations through a 22 gauge needle and then 200 ul of chloroform was added and the sample was incubated on ice for 15 minutes (during this time the sample was vortexed multiple times). Following incubation with chloroform, the sample was centrifuged for 15 minutes at 14,000 rpm and the aqueous layer was removed and ethanol precipitated. This extraction method produces RNA which is primarily derived from cells of epithelial origin. In order to obtain RNA samples which presumably includes RNA derived from these stromal cells; the particulate material (remaining in the pellet from the 30 second centrifugation) was homogenized with a tissuemizer, washed with PBS, treated with collagenase at 37° C. for 30 minutes, sonicated, extracted with phenol/chloroform and ethanol precipitated.

cDNA libraries were constructed in lambda phage using polyA-selected mRNA from the following samples; cultured human breast epithelial cells, tissue from three reduction mammoplasty patients, tissue from three DCIS patients, and tissue from one DCIS patient (patient #10) that showed a focus of microinvasion adjacent to an area of DCIS. Multiple punches were needed to obtain sufficient RNA for polyA selection and library construction. 200 ug of total RNA was obtained by pooling 20 punches from normal breast tissue (reduction mammoplasty samples) and 5–8 punches from DCIS lesions, presumably reflecting the greater cellularity of the DCIS samples. cDNA libraries were constructed by first and second strand cDNA synthesis followed by the addition of directional synthetic linkers (ZAP-cDNA Synthesis Kit, Stratagene, La Jolla, Calif.). The Xho I-Eco R1 Tinkered cDNA was then ligated into lambda arms, packaged with packaging extracts, and then used to infect XL1-blue bacteria resulting in cDNA libraries.

Probe Preparation

The collagen III probe employed for nuclease protection assays was constructed by subcloning the 208 bp Hinc II-Pst I fragment from the 3' untranslated region of the human type III procollagen gene into pGem4Z. This region of the human procollagen III gene was obtained by PCR amplification of published sequence (Ala-Koldco et al, 1989) followed by restriction with Hinc II and Pst I. For a control probe to assure equal loading and recovery of RNA, we used a T7 polymerase-generated probe for human glyceraldehyde phosphate dehydrogenase (GADP) which protects a 140 bp Sac I-Xba I fragment; (a generous gift from Janice Nigro, Vanderbilt University). Probe DCIS-1 was generated by linearizing the rescued plasmid with Pvu II, which should generate a 200 bp protected fragment. RNase protection assays were performed with 1 ug of unselected RNA and the above-cited probes using the methods we have reported previously (Holt, 1993).

Differential Display-based Cloning of cDNAs

Rescued cDNA library samples were used as templates for low stringency PCR with the either a pair of 25 bp primers or an anchored 14 bp primer paired with a random 25 bp primer. Random 25 bp primers were generated by a computer-based algorithm (Jotte and Holt, unpublished). Samples were denatured for two minutes at 95° C. followed by 40 cycles, each cycle consisting of denaturation for 1 minute at 94° C., annealing for 2 minutes at 25° C., and extension for 1 minute at 72° C. The samples were then run on an 6% non-denaturing polyacrylamide gel, which was dried and autoradiographed. Specific bands were excised then reamplified with the same primers used for their generation. Specificity was confirmed on 6% polyacrylamide gel, and samples were purified by ethanol precipitation of the remainder of the PCR reaction. Fragments were then individually cloned into SrfI cut vectors by standard methods using PCR-Script™SK(+) Cloning Kit (Stratagene, LaJolla, Calif.) and then sequenced.

EXAMPLE 1

Studies Showing Increased Risk of Breast Cancer in Patients with DCIS

Since the 1970's, studies of pre-invasive lesions associated with the development of breast cancer have been undertaken in an attempt to refine histologic and cytologic criteria for the hyperplastic lesions analogous to those of the uterine cervix and colon. Because of the availability of tissue from breast biopsies done many years previously, cohorts of women who underwent breast biopsies 15 to 20 years ago, can be studied to determine the risk for development of breast cancer attributable to specific lesions. Many concurrent studies evaluating lesions associated with cancer at time of cancer diagnosis led the way in pointing out lesions of potential interest (Wellings et al, 1975). Hopefully, these intermediate stages in cancer development will serve to provide indicators of breast cancer development sufficiently precise to guide prevention and intervention strategies (Weed et al, 1990; Lippman et al, 1990). Such intermediate elements prior to the development of metastatic capable cancers also provide the opportunity to define the molecular biology of these elements. Studies of the development of pre-invasive breast disease have provided insight into different types of lesions with different implications for breast cancer risk and the process of carcinogenesis (See FIG. 1). Pre-invasive breast disease is herewith defined to be any reproducibly defined condition which confers an elevated risk of breast cancer approaching double that of the general population (Komitowski et al, 1990). The specifically-defined atypical hyperplasias and lobular carcinoma in situ confer relative risks of four to ten times that of the general population. This risk is for carcinoma to develop anywhere in either breast (Page et al, 1985; Page et al, 1991). The statistical significance of these observations have regularly been <0.0001. Thus, absolute risk figures of 10–20% likelihood of developing into invasive carcinoma in 10 to 15 years arise. DCIS is a very special element in this story because the magnitude of risk is as high as any other condition noted (P<0.00005), but remarkably, the developing invasive cancer is in the same site in the same breast. This local recurrence and evolution to invasiveness marks these lesions as determinate precursors of invasive breast cancer (Betsill et al, 1978; Page et al, 1982). These figures are for the type of DCIS which has become detected very commonly since the advent of mammography, the small and NCDCIS variety. It is likely that the comedo DCIS variety indicates a much greater risk, often presenting as larger lesions, and treated regularly by mastectomy in the past 50 years making follow-up studies impossible (FIG. 1).

The precision of histopathologic diagnosis in this area as noted in Table I (shown in FIG. 1) was most convincingly confirmed in a large, prospective study (London et al, 1991). There has also been a recent review of the reproducibility of the assignment of diagnosis by a panel of pathologists (Schnitt et al, 1992). The precision has been fostered by combining histologic pattern criteria with cytologic and extent of lesion criteria. Classic surgical pathology criteria were predominantly derived from histologic pattern only. A further point of relevance to the importance of these histopathologically defined lesions of pre-malignancy in the breast is the relationship to familiarity. A family history of breast cancer in a first degree relatives confers about a doubling of breast cancer risk. However, women with the atypical hyperplasias at biopsy and a family history of breast cancer are at 9–10 times the risk of developing invasive breast cancer as the general population (Dupont et al, 1985; Dupont et al, 1989).

Careful consideration of all of the above-mentioned epidemiologic data has led to the following model for progression from generalized pre-malignant lesions to determinant lesions to invasive cancer. FIG. 2 shows this model for the induction and progression of pre-invasive breast disease based on study of the Vanderbilt cohort (Dupont et al, 1985) of more than 10,000 breast biopsies (follow-up rate 85%; median time of 17 years; 135 women developed breast cancer).

EXAMPLE 2

Identification of Genes Which are Differentially Expressed in DCIS Construction of cDNA Libraries from DCIS Lesions In order to study differential gene expression in DCIS, we collected cases of NCDCIS. The diagnosis of DCIS is made on histomorphologic grounds based on architectural, cytologic, and occasionally extent criteria. NCDCIS lacks comedo features and consists of microscopic intraductal lesions which fill and extend the duct, contain rigid internal architecture, and often have hyperchromatic and monomorphic nuclei.

Study of non-comedo DCIS for differential marker gene expression indicates the diagnostic utility of comparison of marker gene expression in these tissues. Although the morbidity and mortality of breast cancer clearly results from invasion and metastasis, the development of breast cancer is clearly significant in its early stages for two basic reasons:

1) The molecular changes will presumably be simpler in early lesions than in later lesions which may have acquired numerous mutations or "hits"; and
2) Successful prevention strategies may require attacking cancer before it develops the capacity to invade or metastasize.

Non-comedo DCIS is the earliest determinant lesion which recurs locally as invasive cancer. Although comedo DCIS may be technically easier to study because the tumors are larger, its aggressiveness and the presence of numerous genetic alterations (such as p53 and erbB2) suggest that it may have advanced beyond the earliest stages of carcinogenesis.

The commercial utility of a method for prevention of cancer is clear. In order to study differential gene expression in DCIS, breast tissue with extensive microscopic non-comedo DCIS was identified and banked in a frozen state. cDNA libraries were constructed from mRNA isolated from frozen sections of DCIS lesions. Tissue samples from patients with mammographic results consistent with DCIS were cryostat frozen and a definitive diagnosis was made by the histopathologic criteria which we have described (Jensen et al, Submitted for publication; Holt et al, In press).

Figure 3:
FIG. 3 presents photographs of DCIS tissue, before (upper left panel) and after microscopically-directed excisional punch biopsy (upper right panel). The lower panells show tissue samples of normal breast tissue (lower left panel), and invasive breast cancer (lower right panel).

Control mRNA was obtained from frozen tissue samples obtained from reduction mammoplasties and from cultured human breast epithelial cells. Because non-comedo DCIS is a microscopic lesion, we had to microlocalize regions of DCIS in biopsy samples. To accomplish this we prepared frozen sections in which we located regions of DCIS and then employed a 2 mm punch to obtain an abnormal tissue sample only from those regions that contained DCIS. This selective harvesting was accomplished by carefully aligning the frozen section slide with the frozen tissue block and identifying areas of interest. The harvest of the appropriate area was then confirmed with a repeat frozen section. A similar approach was used to isolate mRNA from lobules of normal breast in samples collected from a reduction mammoplasty. Prior studies have shown that breast lobules are approximately 2.5 mm in diameter, thus the 2 mm punch provided a well-tailored excision. This microlocation and collection step, in which abnormal tissue samples are collected from an isolatable tissue structure, was performed with extreme care and was absolutely crucial to the success of these studies. Contamination by normal breast epithelial cells or by breast stromal cells would clearly negatively skew the differential screening approach. If the punch biopsy did not cleanly excise DCIS without contamination by other cell types or tissues then the sample was not used for mRNA isolation (Jensen et al, Submitted for publication). FIG. 3 contains color photos of DCIS (abnormal) tissue, before (upper left panel) and after excisional punch biopsy (upper right panel). The lower panels show tissue samples of normal breast tissue lower left panel), and invasive breast cancer lower right panel).

Following microlocation punch harvesting of the frozen tissue, RNA was isolated, purified, and employed to construct cDNA libraries. RNA was isolated following mincing of tissue in 5.6M guanidinium isothiocyanate and 40% phenol, centrifugation to remove particulate matter, viscosity reduction by repeated aspiration through a 22 gauge needle, chloroform extraction and ethanol precipitation. In most samples there was particulate matter resistant to guanidinium-phenol extraction that was white in color and fibrous in appearance and was presumed to represent breast stroma. This stromal material was sparse in DCIS samples but abundant in samples obtained from normal breast tissue derived from reduction mammoplasties. The stromal material was minced with a tissuemizer, washed with PBS, treated with collagenase at 37° C. for 30 minutes, sonicated, extracted with phenol/chloroform and ethanol precipitated. 200 ug of total RNA was obtained by pooling 20 punches from normal breast tissue (reduction mammoplasty samples) and 5–8 punches from DCIS lesions, presumably reflecting the greater cellularity of the DCIS samples. All libraries had greater than 50% inserts and contained between $2 \times 10^6$ and $7 \times 10^7$ phage recombinants with an average insert size varying between 500 and 1000 base pairs.

EXAMPLE 3

Development of an Extraction Method Which Produces Breast Epithelial RNA

Figure 4:
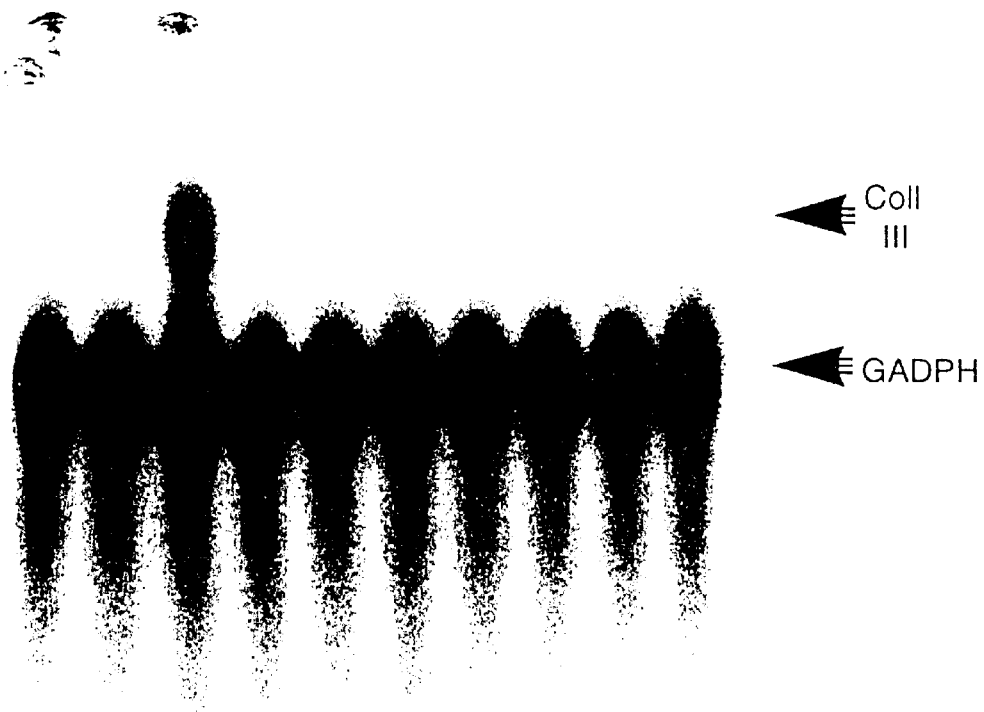
FIG. 4 shows expression of collagen III mRNA in tissue mRNA samples, analyzed by RNase protection assay methods. One ug of mRNA was hybridized with two labeled RNA probes: a T7 polymerase-generated probe for human glyceraldehycle dehydrogenase (GADP) which protects a 140 bp Sac I-Xba fragment; and a 17 polymerase-generated probe which protects a 208 bp Hinc II-Pst I fragment from the 3' untranslated region of the human type III procollagen gene (Coll III) obtained by PCR subcloning the published sequence (Ala-Kokko, 1991). RNA samples were labeled as follows: NL1 is RNA from cultured human breast epithelial cells (Hammond et al., 1984), NL2 is RNA from normal breast tissue, NL3 is RNA derived from the fibrous stromal fraction of breast tissue as described (Jensen et al., submitted for publication), NL4 is another sample from normal breast tissue. #12, #8, #4, #6, #10 are from patient samples with DCIS. Sample #10CA is RNA obtained from the small focus of microinvasion shown in FIG. 3 in the upper right panel. Con is a control sample using tRNA.

It was necessary that tissue samples not be contaminated by non-epithelial stromal cells. Such contamination would complicate efforts to compare gene expression between samples. In order to test the extent of stromal contamination of the mRNA samples, we determined the level of expression of collagen III mRNA by an RNase protection assay. RNase protection assays were employed in these and subsequent studies because it is a quantitative method and can be performed on small amounts of unselected RNA. Collagen III mRNA was identified in the presumed stromal fraction of the normal breast tissue and to a lesser extent in the microinvasive breast cancer sample, but no expression of collagen III was detected in the DCIS samples which were subsequently employed for cDNA library construction. FIG. 4 compares expression in NL 2 and #10CA with other patient samples and NL1 to determine collagen III expression.

Expression of Collagen III mRNA in tissue mRNA samples was analyzed by RNase protection assay by methods we have reported previously (Holt, 1993). One $\mu$g of mRNA was hybridized with two labeled RNA probes: a T7 polymerase-generated probe for human glyceraldehyde phosphate dehydrogenase (GADP) which protects a 140 bp Sac I-Xba I fragment; and a T7 polymerase-generated probe which protects a 208 bp Hinc II-Pst I fragment from the 3' untranslated region of the human type III procollagen gene (Coll III) obtained by PCR subcloning of the published sequence (Ala-Kokko et al, 1991). RNA samples were labeled as follows: NL1 is RNA from cultured human breast epithelial cells (Hammond et al, 1984), NL2 is RNA from normal breast tissue, NL3 is RNA derived from the fibrous stromal fraction of breast tissue as described (Jensen et al, Submitted for publication), NL4 is another sample from normal breast tissue. This is described in greater detail on page 30 of this patent application. #12,#8,#4,#6, and #10 are from patient samples with DCIS. Sample #10CA is RNA obtained from the small focus of microinvasion shown in FIG. 3. Con is a control sample using tRNA.

EXAMPLE 4

Screening of cDNA Libraries

Following successful testing which demonstrated that stromal contamination was not a problem, cDNA libraries were constructed in lambda phage using polyA-selected mRNA from the following samples: cultured human breast epithelial cells, tissue from three reduction mammoplasty patients, tissue from three DCIS patients, and tissue from one DCIS patient (patient #10) that showed a small focus of invasion adjacent to an area of DCIS. Multiple punches were needed to obtain sufficient RNA for polyA selection and library construction. Selective handling of tissue was accomplished.

Figure 5:
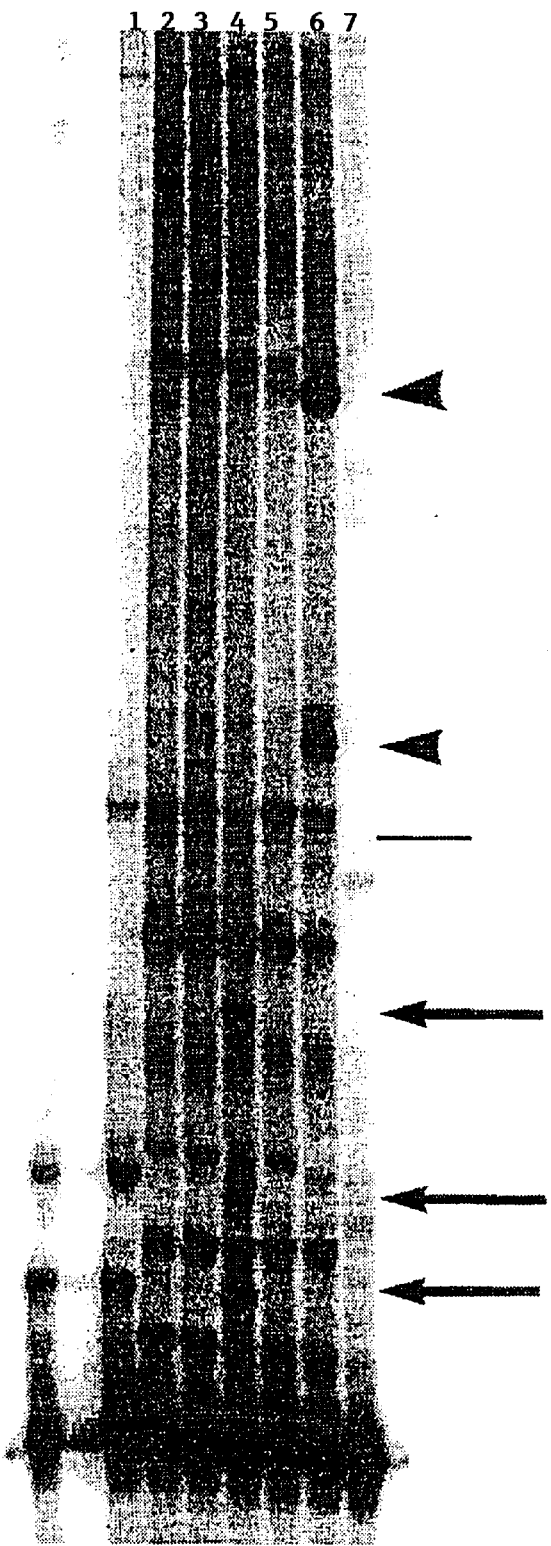
FIG. 5 shows differential display of cDNAs obtained from patient tissue samples and controls. Rescued cDNA library samples were used as templates for low stringency PCR with the primers 5'GATGAGTTCGTGTCCGT ACAACTGG-3' (SEQ ID NO:54) and 5'GGTTATCGAAATCAGCCA-CAGCGCC (SEQ ID NO:55); 40 cycles were performed with denaturation for 1 minute at 94° C., annealing for 2 minutes at 25° C., and extension for 1 minute at 72° C. The samples correspond to those in the legend to FIG. 5: Lane 1 is #12; Lanes 2 and 3 are from separate phage rescues of NL1 to show reproducibility of the assay; Lane 4 is #8; Lane 5 is #10; Lane 6 is #10CA; Lane 7 is a control from the rescued phage vector without cDNA inserts. Arrows mark cDNAs which are overexpressed in DCIS versus normal and arrowheads mark cDNAs which are differentially expressed in the invasive cancer (note this may reflect contamination from stromal cells as shown in FIG. 3). The bar marks a cDNA which is expressed in normal breast cells at higher levels than in DCIS or invasive cancer.

Comparison of gene expression between samples was performed by either differential screening or a modification of differential display (Liang et al, 1992a; Liang et al, 1992b; Saiki et al, 1988; Melton et al, 1984). Plasmid DNA was prepared from the cDNA libraries following helper phage rescue and screened by two independent methods. FIG. 5 below shows the results of differential display comparing cDNAs of several patient DCIS samples with cDNA obtained from normal breast epithelial cells and an early invasive cancer. Although few genes shown in this Figure are differentially expressed in the majority of samples with DCIS, the heterogeneity of gene expression in patient samples is seen.

The differential display method (Liang et al, 1992a and 1992b) allows simultaneous comparison of multiple tissue samples. Initial studies using this method (reverse transcriptase followed by PCR) were unsatisfactory because of unwanted amplification of contaminating DNA in tissue samples and the small size of many of the fragments identified by display. To circumvent some of these problems, we have attempted to combine the advantages of cDNA library screening with the advantages of differential display by:

1) Constructing cDNA libraries from the tissue mRNA samples;
2) Performing differential display on the plasmid DNA prepared from the cDNA libraries;
3) Subcloning the fragments identified by differential display;
4) Using the subcloned fragment as a probe to clone the cDNA from the appropriate library.

EXAMPLE 5

Identification of a Gene (RibRed) Which is Differentially Expressed in Multiple NCDCIS Cases Employing these methods, 10 differentially expressed clones were identified and the seven that showed the greatest difference in expression between multiple samples were further characterized by DNA sequencing. Comparison of the sequenced clones with GenBank demonstrated that six of the clones are apparently unique sequences (although further DNA sequencing is necessary); but that one of the clones (here termed DCIS-1 and described in Sequence Listing No. 1) showed 90% homology to the previously cloned hamster gene encoding the M2 subunit of ribonucleotide reductase (Pavloff et al, 1992; Hurta et al, 1991; Hurta et al, 1991). Although human M2 ribonucleotide reductase has been cloned previously, comparison of the hamster cDNA sequence with our clone and with the prior human clone indicates that DCIS-1 is homologous to an alternatively poly-adenylated form of the human ribonucleotide reductase which has not been cloned previously. FIG. 6 shows a comparison of the sequence between DCIS-1 and the human and hamster genes.

Because of our concern that different patients may have differential gene expression which is idiosyncratic (or related to morphological differences in biopsy appearance) and not necessarily related to the induction or progression of DCIS, we simultaneously analyzed gene expression in multiple DCIS samples compared to multiple control samples. We constructed cDNA libraries from the following samples:

1) Cultured HMEC epithelial cells;
2) Reduction mammoplasty: 11 year old with virginal hyperplasia;
3) Reduction mammoplasty: 28 year old patient;
4) Reduction mammoplasty: 35 year old patient;
5) DCIS patient #12;
6) DCIS patient #8;
7) DCIS patient #10;
8) DCIS patient #10 from an area of invasive cancer adjacent to DCIS;

In addition to the samples we employed to construct cDNA libraries shown above, we also obtained frozen tissue samples from 7 more DCIS patients, 2 cellular fibroadenoma samples, and samples of "usual hyperplasia" and atypical hyperplasia.

Figure 7:
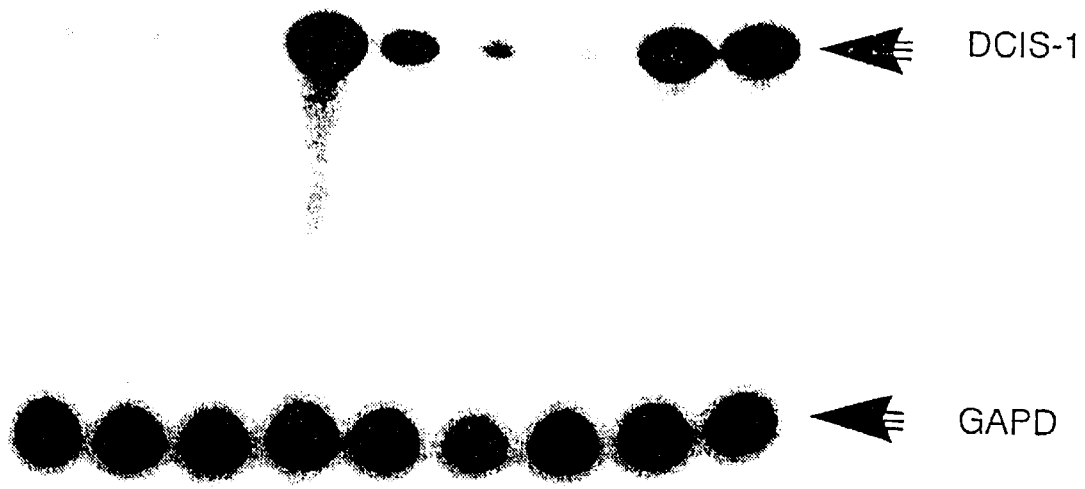
FIG. 7 shows expression of DCIS-1 mRNA in tissue mRNA samples analyzed by RNase protection assay as described in the legend to FIG. 4. The GADH probe and a probe for the clone DCIS-1, which was generated by linearizing the rescued plasmid with Pvu II, were used and should generate a 200 bp protected fragment was used. RNA samples were labeled as in the legend to FIG. 4.

Because the DCIS clones were identified by cloning methods which include selection and amplification, it was important to confirm by nuclease protection assays that the genes were differentially expressed in the original unselected, unamplified RNA samples (FIG. 7).

This approach allowed identification of a human gene similar to the hamster RibRed gene (coding for the M2 subunit) and 7 other human genes as genes which are differentially expressed in a majority of cases of DCIS in human breast tissue. The table of differentially expressed genes lists the genes which have been identified as differentially expressed genes in DCIS tissue samples as compared to that in normal tissue (FIG. 9).

EXAMPLE 6

Methods for Studying Potential Use of Differentially Expressed Genes for Diagnostic Screening One advantage of the differential display method is that it allows comparison of multiple tissue samples of pre-invasive or invasive breast cancer. For example, use of this method has successfully demonstrated that the M2 subunit ribonucleotide reductase gene is differentially expressed in 4 out of 5 pre-invasive breast cancer tissue samples. It is significant that the M2 subunit is involved in the regulation of the ribonucleotide reductase gene and is found to be over-expressed in abnormal tissue samples.

Identification of differentially expressed genes may lead to discovery of genes which are potentially useful for breast cancer screening. Of particular interest are genes whose expression is restricted to breast epithelial cells and whose gene products are secreted. Screening for secreted proteins is possible by using the known hydrophobic sequences which encode leader sequences as one primer for differential display. The identification of secreted proteins which are specific for early breast pre-malignancy (or even early invasive cancer) would provide an important tool for early breast cancer screening programs. If a differentially expressed gene has not been cloned previously (or if details of its expression are unknown or uncertain) then nuclease protection assays or Northern blots can be performed on RNA prepared from tissue samples from a variety of tissues to determine if expression of this gene is restricted to breast. If necessary cDNA libraries prepared from other tissues can be added to the differential display screen as a way to identify only those genes which are expressed in early breast cancer and, in addition, are only expressed in breast tissue.

Once differentially expressed genes have been initially characterized for expression in pre-malignant and malignant breast disease, antibodies to the protein products of potentially useful genes can be developed and employed for immunohistochemistry (Harlow et al, 1988). This will provide an additional test to determine whether the expression of this gene is restricted to the breast. Subsequently, these antibodies will be used to detect the presence of this protein present in the blood of patients with pre-invasive and/or invasive cancer. By assaying for serum protein levels in the same patients who exhibited elevated expression of the gene in their tissue samples it will be possible to determine whether a gene product is being secreted into the blood.

EXAMPLE 7

Decreased Expression of BRCA1 Accelerates Growth and is Observed During Breast Cancer Progression Breast cancer occurs in hereditary and sporadic forms. Recently the BRCA 1 gene has been cloned and shown to be mutated in kindreds with hereditary breast and ovarian cancer (Hall et al. 1990, Miki, Y. et al. 1994, Friedman et al. 1994, Castilla et al. 1994, Simard et al. 1994). Although 92% of families with two or more cases of early-onset breast cancer and two cases of ovarian cancer have germ-line mutations in BRCA 1 (Narod et al. in press), the gene has not been shown to be mutated in any truly sporadic case to date (Futreal et al. 1994). Despite the surprising paucity of somatically acquired mutations in sporadic breast cancer, it is still a likely tumor suppressor gene with a key role in breast epithelial cell biology. The BRCA 1 gene encodes a protein of 1863 amino acids with a predicted zinc finger domain observed in proteins which regulate gene transcription.

As an initial characterization of the regulation and function of the BRCA 1 gene, we analyzed and manipulated expression of BRCA 1 mRNA levels. The results taken together indicate that the BRCA 1 gene product is a negative regulator of mammary cell proliferation which is expressed at diminished levels in sporadic breast cancer.

Expression of BRCA1 mRNA During Breast Cancer Progression

As described above, microscopy-directed cloning has been employed to compare gene expression in normal mammary epithelium, carcinoma in-situ, and invasive breast cancer. This method produces predominantly epithelial mRNA with minimal contamination from stromal elements and we used this approach to obtain mRNA from normal neoplastic tissues from patients without a family history of breast cancer. Expression of BRCA1 exon 24 in human breast tissue samples is shown in FIG. 1. The legend of FIG. 1 is as follows.

The following tissue samples were used for mRNA isolation: Normal tissue samples: NL1-cultured human breast epithelial cells, NL2-Histologically normal breast tissue from an 11 year old undergoing a reduction mammoplasty, NL4-histologically normal breast tissue from an 14 year old undergoing a reduction mammoplasty. Carcinoma-in-situ samples are #6, #8, #10, #12, #23 (comedo type), #41, #55; and invasive cancer samples #10CA (invasive from the same patient with carcinoma-in-situ), 36CA, 1CA. All of these tissue samples were obtained from patients who had no family history of hereditary breast cancer and RNA preparation was performed as described above.

Figure 10A:
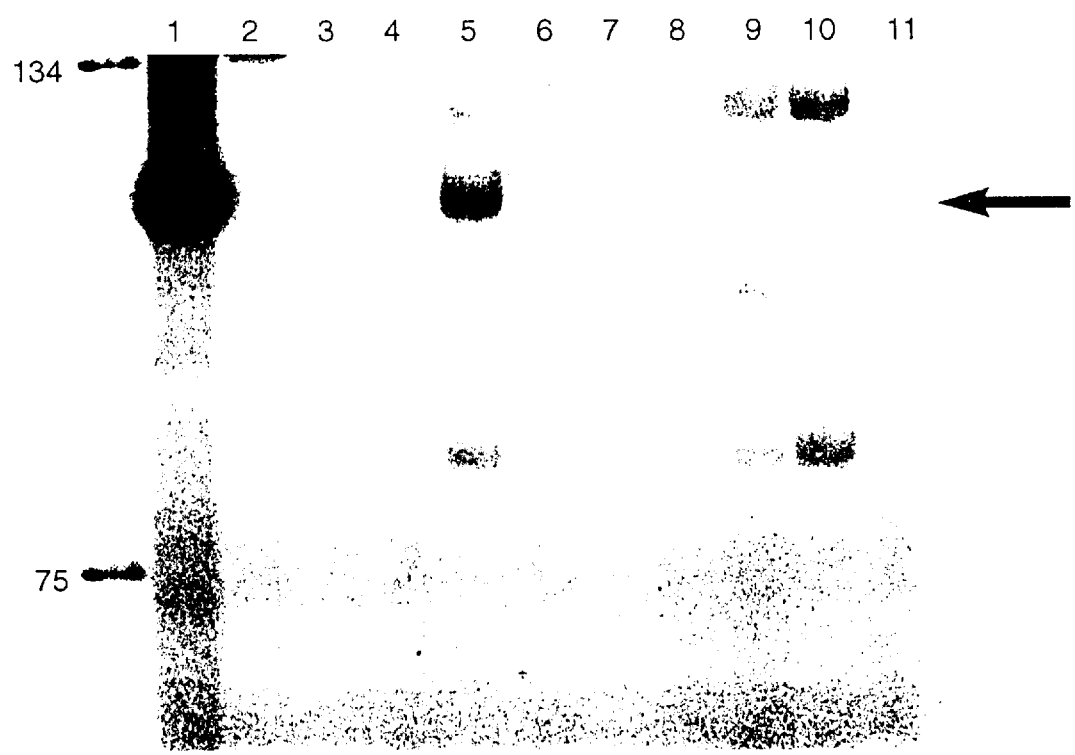
FIGS. 10A and 10B shows expression of BRCA1 mRNA during breast cancer progression by PCR detection and nuclease protection assay, respectively.

PCR detection of BRCA1 exon 24 in cDNA libraries from the following tissue samples is described in FIG. 10A. Lane 1: human genomic DNA, lane 2: NL1, lane 3: NL4, lane 4: $8, lane 5: #12, lane 6: #10, lane 7: #10CA, lane 8: #41, lane 9: #23, lane 10: 36CA, lane 11: lambda DNA. The arrow points to the expected 113 bp band.

Figure 10B:
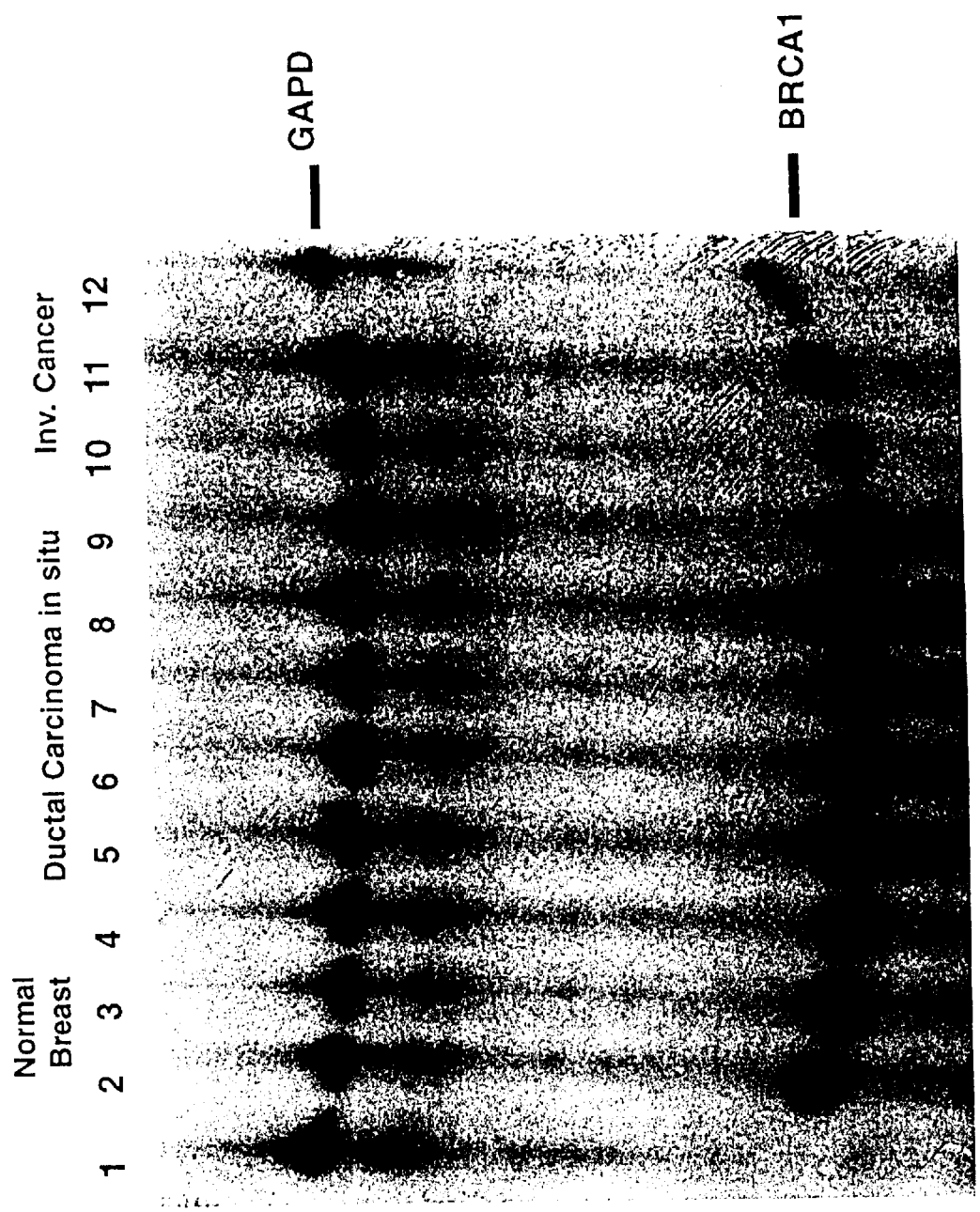

Nuclease protection assays of microdissected mRNA from tissue samples are described in FIG. 10B. One ug of mRNA from each tissue sample was hybridized with 32P-labelled, T7 polymerase-generated RNA probes for BRCA1 and human glyceraldehyde-3-phosphate dehydrogenase (GAPD) which produce expected protected fragments of 113 and 140 respectively as indicated by the lines on the right. Data were quantitated by phosphorimaging. The hybridizing intensity of each BRCA1 band was normalized to its respective GAPD band. The normalized values of NL1, NL2, and NL4 were intensity in each sample relative to 1. Sample 1 employs human leukocyte mRNA; Samples 2–4 are NL1, NL2, and NL4A; Samples 5–9 are #6(2.8), 8(3.7), 10(2.8), 12 (5.9), and 55 (1.4); and 10–12 are #10CA (0.07), 36CA (0.13), and 1CA (0.2).

FIG. 10 shows that BRCA1 exon 24 mRNA is expressed at 5–10 fold higher levels in normal mammary tissue than in invasive breast cancer samples. Initial studies showed detectable levels of BRCA1 cDNA in a cDNA library prepared from a tissue sample with preinvasive carcinoma-in-situ but not in normal breast cancer invasive breast cancer cDNA libraries (FIG. 10A). Because this method is relatively insensitive we directly quantitated BRCA1 mRNA by nuclease protection assays in RNA samples obtained by our microdissection method described above. These assays indicate that expression of BRCA1 mRNA in micro-dissected normal mammary epithelial tissue (lanes 2–4, FIG. 10B) is 5–15 fold higher than that in breast cancer (lanes 10–12, FIG. 10B). The highest levels of BRCA1 are observed in samples from non-comedo ductal carcinoma-in-situ (lanes 5–9, FIG. 10B), a premalignant breast lesion with a finite, but relatively low rate of progression to invasion (Betsill et at., 1978, Page, D. L. et al., 1982, Page and Dupont, 1990).

Because these studies suggested that invasive breast cancer exhibited lower mRNA levels than normal breast epithelial cells, we compared expression of paired samples of normal breast and invasive cancer from the same patient (FIG. 11 A; compare lanes 2 and 3, 4 and 5, 6 and 7). The legend of FIG. 11 is as follows.

Figure 11A:
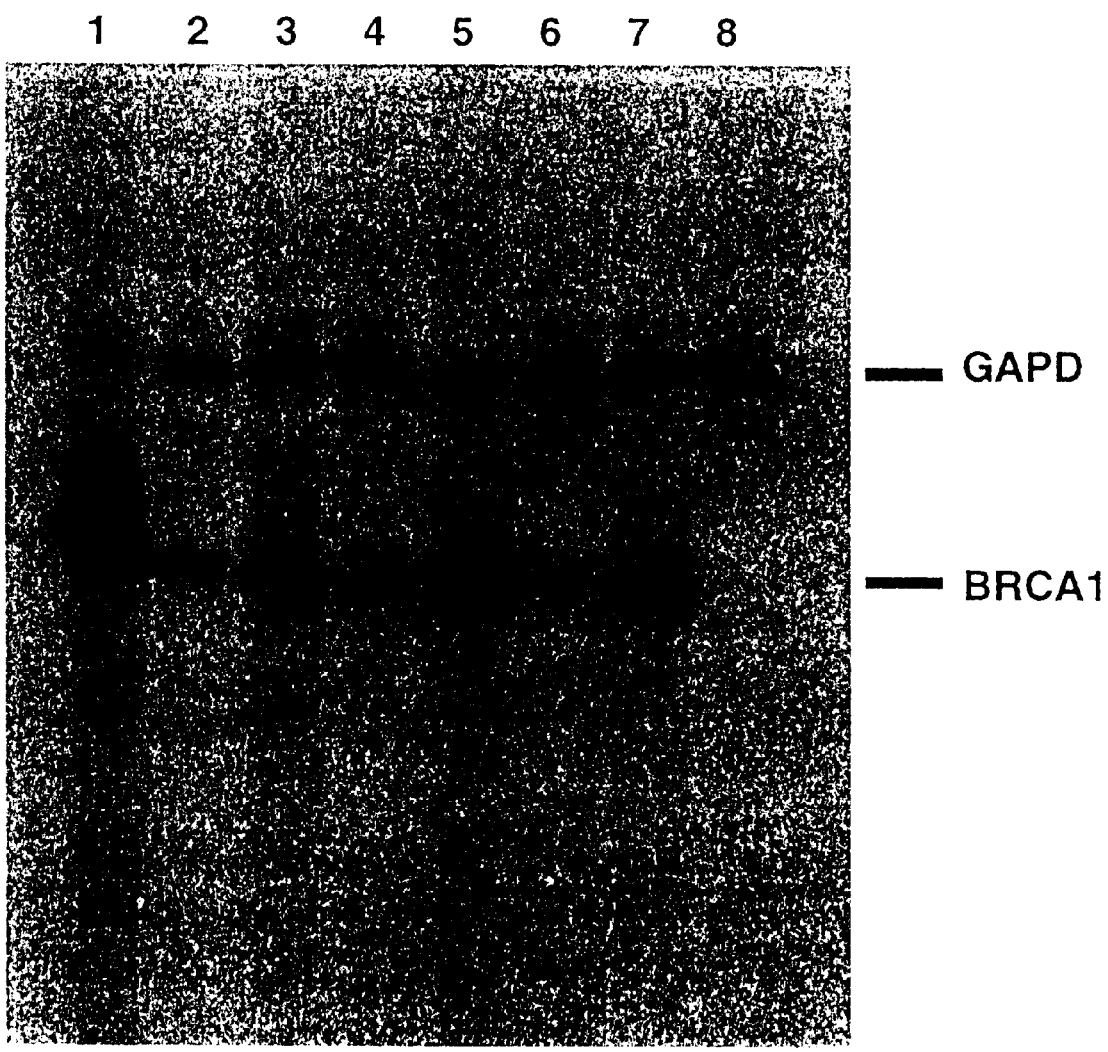
FIGS. 11A and 11B is a comparison of BRCA1 expression in normal breast and invasive breast cancer using nuclease protection assay of RNA, respectively.

Nuclease protection assays of RNA obtained from paired samples of invasive breast cancer and histologically normal breast tissue are shown in FIG. 11A. Samples in lanes 2 and 3 (first patient), 4 and 5 (second patient), 6 and 7 (third patient) are from invasive cancer and normal breast tissue respectively. Lane 1 is NL1 mRNA as described in legend to FIG. 10 and lane 8 is human leukocyte mRNA. Ratios of BRCA1/GAPD for each sample: lane 1: 25.9, lane 2: 1.8, lane 3: 7.6, lane 4: 2.0, lane 5: 12.4, lane 6: 0.7, lane 7: 6.0. The probes and methods are as described in FIG. 10 except the GAPD probe was of lower specific activity to improve quantitation.

Figure 11B:
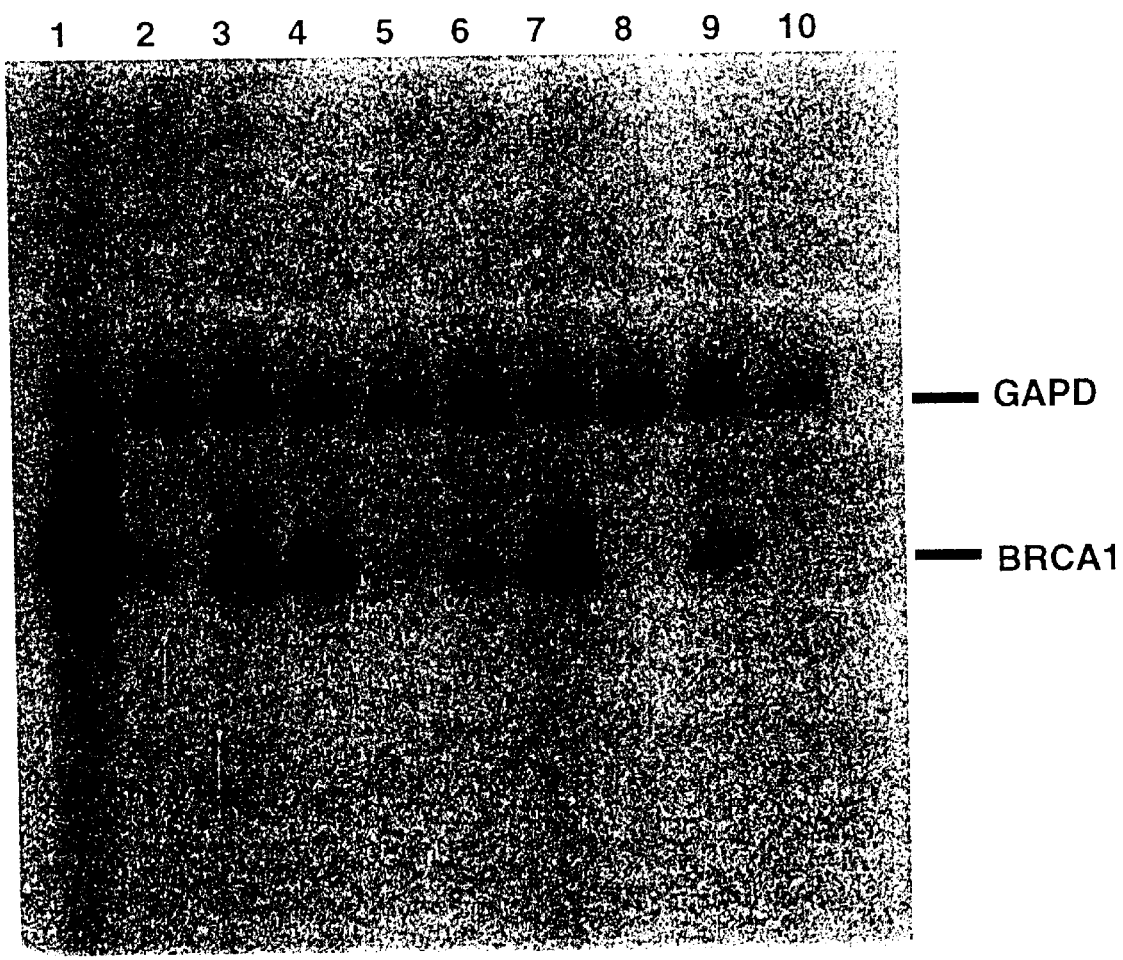

Nuclease protection assays of RNA from a series of invasive breast cancer tissue samples (lanes 2–9 compared with NL1 (lane 1) and leukocyte mRNA (lane 10) are shown in FIG. 11B. Ratios of BRCA1/GAPD for each sample: lane 1: 19.1, lane 2: 0.3, lane 3: 1.8, lane 4: 1.6, lane 5: 0.2, lane 6: 0.3, lane 7: 1.9, lane 8: 0, lane 9: 0.6.

Although the samples were paired in FIG. 11A, they were not microdissected so this approach overestimates the relative expression level of invasive samples because they have a greater percentage of epithelial cells. RNA levels were four to eight fold higher in samples derived from normal breast than in samples derived from invasive breast cancer. We next analyzed expression levels in 8 non-hereditary invasive cancer samples (FIG. 11B: lanes 2–7). Although these samples showed some variability in expression level, all had lower levels of BRCA1 mRNA (determined by ratio of BRCA1 to GAPD) than the primary breast epithelial cell line or the normal breast samples shown in FIG. 11A.

Effects of BRCA1 Gene Inhibition on Proliferative Rate and Gene Expression

Figure 12A:
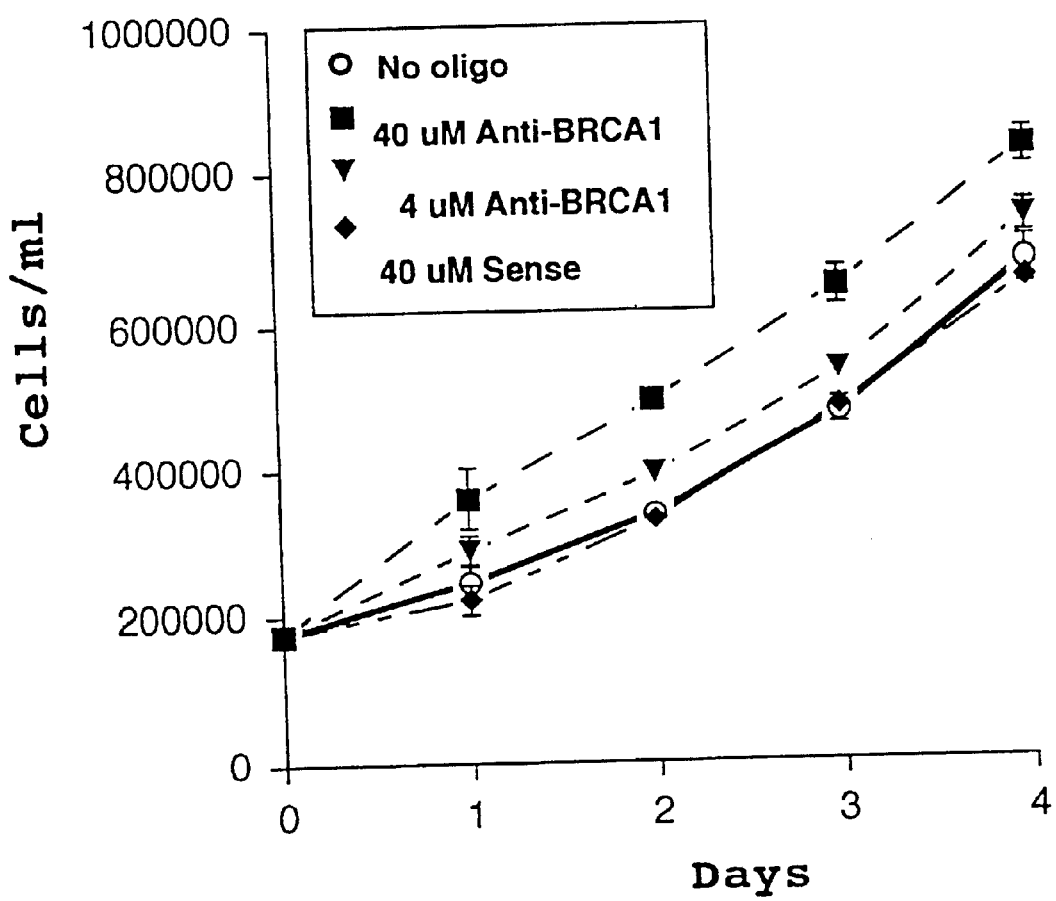
FIGS. 12A, 12B, and 12C show that antisense inhibition of BRCA1 accelerates mammary cell proliferation.
Figure 12B:
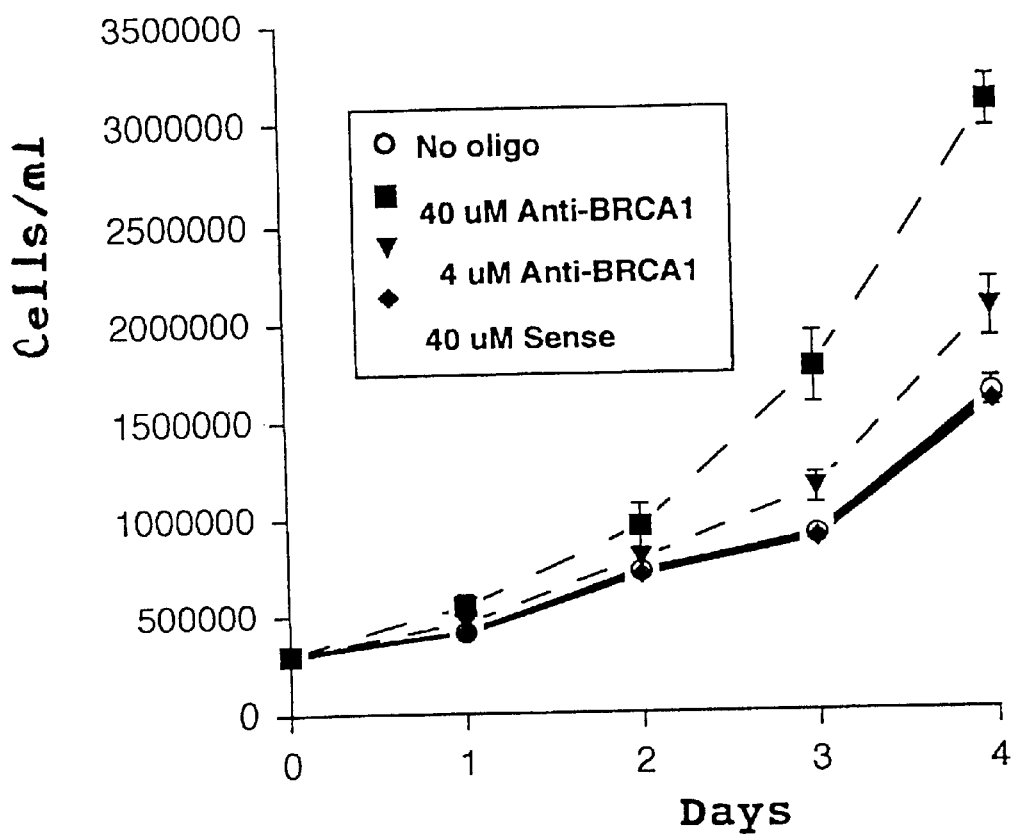

Having demonstrated that mRNA expression levels of BRCA1 are higher in normal mammary cells than in cancer cells, we used antisense methods to test the hypothesis that BRCA1 expression inhibits cell growth. Unmodified 18 base deoxyribonucleotide complementary to the BRCA1 translation initiation site were synthesized and added to cultures of primary mammary epithelial cells (Stampfer et al. 1980) or MCF-7 breast cancer cells (Soule and McGrath, 1980). FIG. 12 is graph showing growth rate of human primary mammary epithelial cells (A), MCF-7 cells (B), retinal pigmented epithelial cells (C), cultured as described below. Points and bars represent the mean and the 95% confidence interval of triplicate counts of cells incubated with a single bolus of the indicated concentration of antisense or control sense deoxyribonucleotide.

Figure 12C:
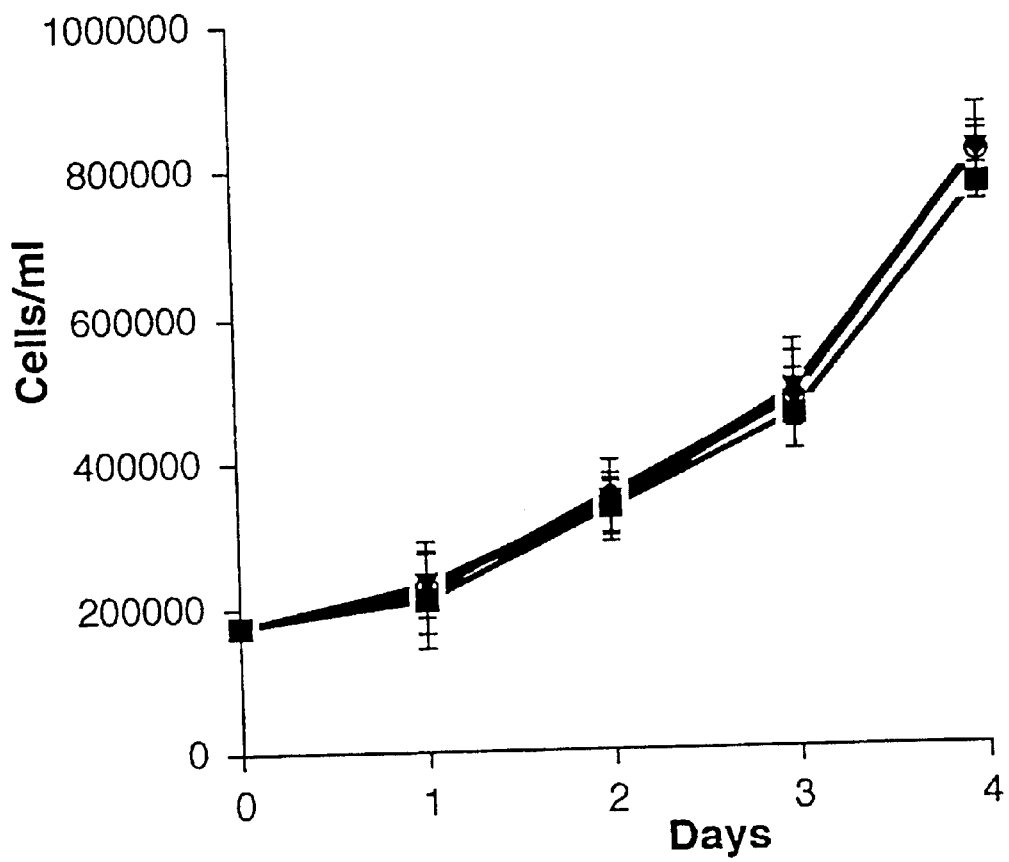

The morphologic appearance of the cell lines was not noticeably changed by addition of antisense oligonucleotide, but the proliferative rate was faster. Incubation of cells with 40 uM anti-BRCA1 oligonucleotide produced accelerated growth of both normal (FIG. 12A) and malignant mammary cells (FIG. 12B), but did not affect the growth of human retinal pigmented epithelial cells (FIG. 12C). An intermediate dose of anti-BRCA1 oligonucleotide produced a less pronounced but significant increase in cell growth rate. This was not a toxic effect of the oligonucleotide since a control "sense" oligomer with the same GC content did not increase the proliferation rate, and because an addition of a 10 fold excess of sense oligomer to the anti-BRCA1 oligomer reversed the growth activation.

In order to critically evaluate the function of BRCA1 gene inhibition on growth stimulation and cell cycle progression it was necessary to identify a gene whose expression is cell cycle regulated in human mammary cells. The gene encoding the M2 subunit of ribonucleotide reductase is amplified in conditions of nucleotide starvation (Hurta and Wright 1992) and as shown above, exhibits elevated levels of expression in premalignant breast disease. Because ribonucleotide reductase constitutes the rate limiting step in DNA synthesis, we reasoned that it might be cell cycle regulated in a synchronous growth model such as MCF-7 cells which can be growth arrested by tamoxifen and then restimulated by estrogen (Aitken et al. 1985, Arteaga et al. 1989). MCF-7 cells were growth arrested by tamoxifen for 48 hours and then stimulated at time zero (0) with 1 uM estradiol (+E) or control vehicle (–E). Inhibition of DNA synthesis by tamoxifen and induction of synthesis by estrogen were confirmed by nuclear labelling studies with tritiated thymidine.

Figure 13A:
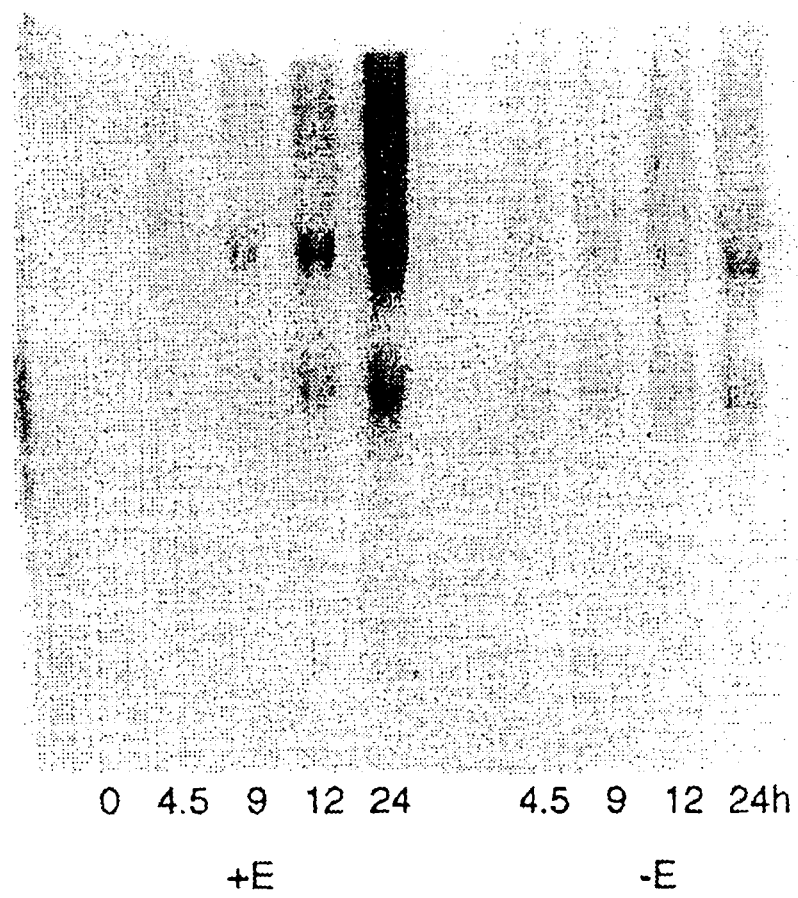
FIGS. 13A and 13B includes a Northern blot of mRNA and nuclear run on studies that show that ribonucleotide reductase M2 mRNA is cell cycle regulated in MCF-7 cells.

FIG. 13 panels A and B show that transcription of the ribonucleotide reductase M2 gene is cell cycle regulated, inhibited by tamoxifen, and induced by estrogen. FIG. 13A is a Northern blot of mRNA from synchronized MCF-7 cells. At the indicated time in hours, total cellular RNA was isolated and Northern blotting performed using the 1.6 Kb Eco RI fragment from our cloned human ribonucleotide reductase cDNA described above. Two mRNA species of 1.6 and 3.4 Kb are observed in these studies.

Figure 13B:
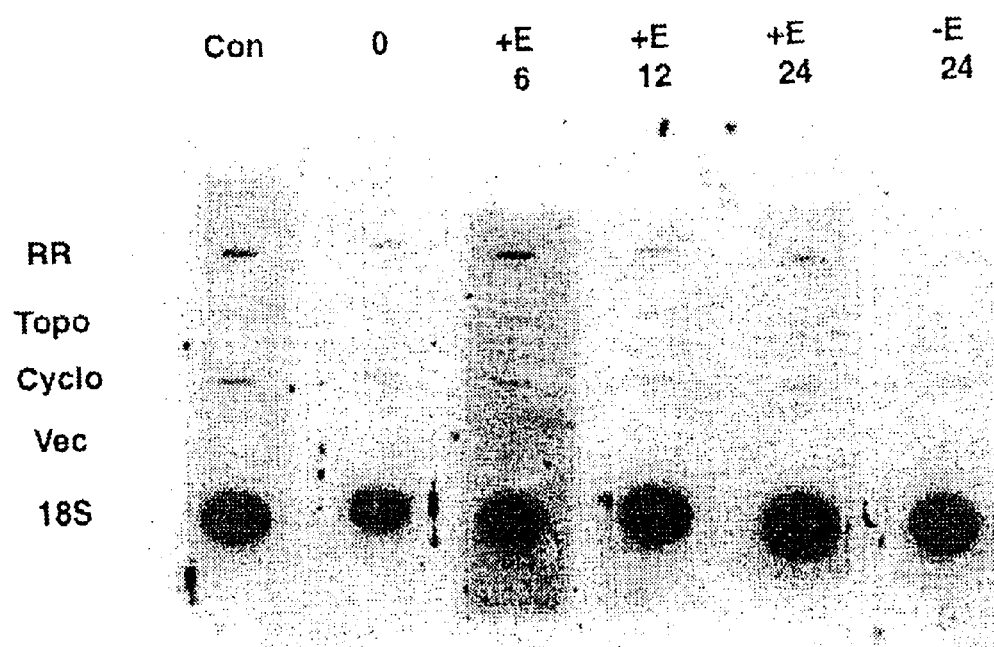

FIG. 13B shows nuclear run on studies of synchronized MCF-7 cells were performed by our published methods (Holt et al 1988) employing the 1.6 Kb fragment of ribonucleotide reductase described above (RR); the 1.8 Kb fragment of Topoisomerase II (Topo) described in the Olsen et al. 1993); the 1.0 Kb cyclophilin gene (Thompson et al. 1994) used as a constitutive control; and 18S ribosomal RNA (Thompson et al. 1994). Con represents cells which were grown for 48 hours but not treated with tamoxifen.

Figure 14:
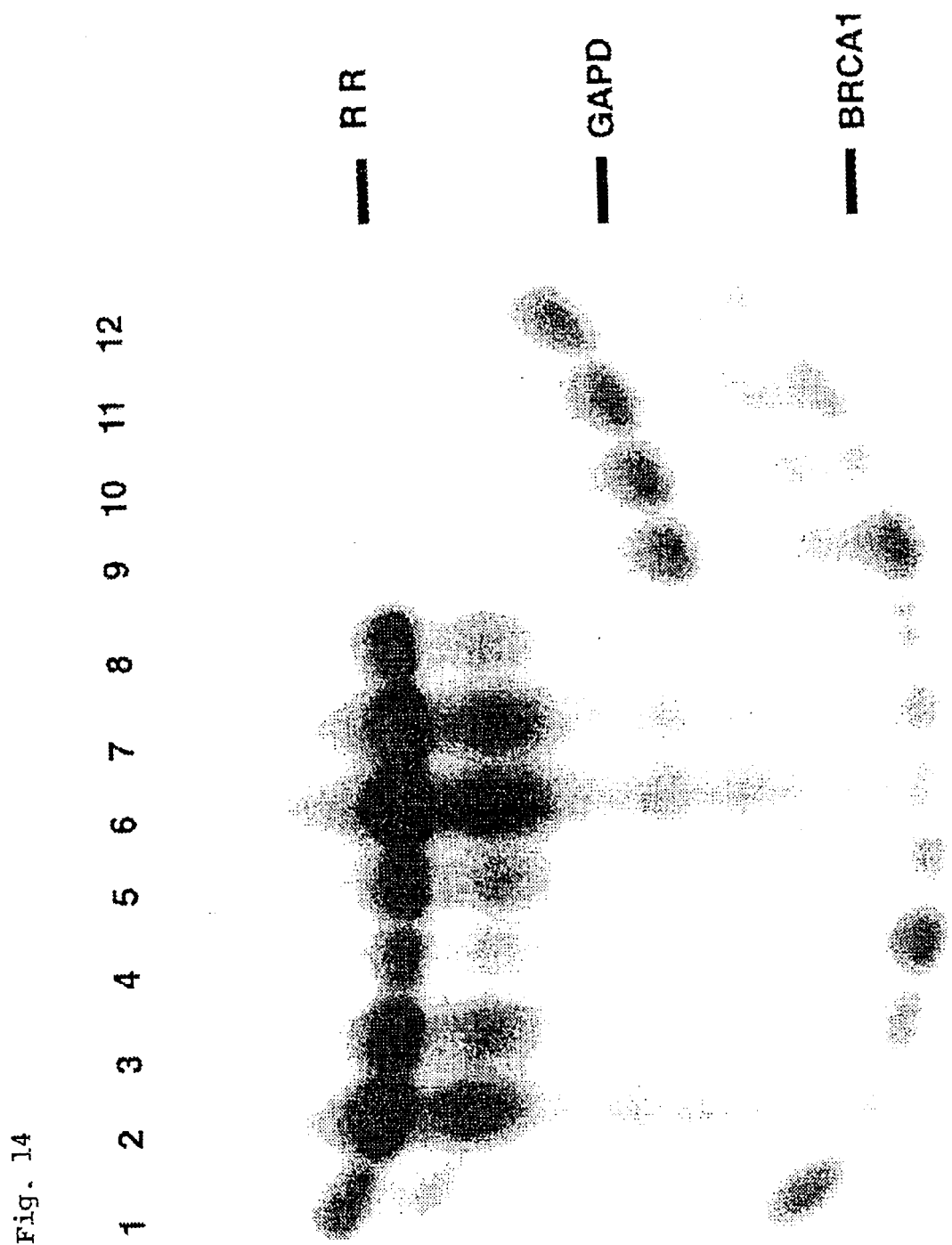
FIG. 14 includes a nuclease protection assay that shows that antisense inhibition of BRCA1 in human mammary cells decreases BRCA1 mRNA and increases ribonucleotide reductase mRNA.

Antisense inhibition is a useful strategy for studying gene expression which is dependent on expression of the antisense target gene (Robinson-Benion and Holt, in press, 1995), e.g. genes whose expression is directly or indirectly dependent on BRCA1 levels. FIG. 14 demonstrates that antisense inhibition of BRCA1 results in a corresponding increased expression of M2 ribonucleotide reductase mRNA. A nuclease protection assay of mRNA derived from primary mammary epithelial cells (lanes 1–4, 9–10) or MCF-7 cells Oanes 5–8, 11–12) cultured for 4 days with antisense or control oligonucleotide was performed under the following conditions: no oligonucleotide (lanes 1 and 5); 40 uM antiBRCA1 (lanes 2,6,10,12); 4 uM antiBRCA1 (lanes 3 and 7); 40 uM sense control (lanes 4,8,9,11). Probes for BRCA1 and GAPD are as described for FIG. 10, and the ribonucleotide reductase M2 probe (RR) detects the 200 bp probe is described above.

Ribonucleotide reductase mRNA levels are highest in samples treated with 40 uM anti-BRCA1 oligonucleotide for both primary mammary epithelial cells and for MCF-7 cells (FIG. 14). Antisense inhibition of BRCA1 results in a 70–90% inhibition of mRNA levels in anti-BRCA1 treated cells compared with cells treated with the "sense" control oligonucleotide (compare lanes 9 and 10, FIG. 14). Note that MCF-7 cells have lower levels of BRCA1 than the normal mammary epithelial cells (compare lanes 1 and 5, FIG. 14) anti-BRCA 1 since the antisense inhibition may drop BRCA1 levels below a critical threshold which normally functions to inhibit growth.

Methodology

Tissue samples. Freshly obtained breast biopsy or reduction mammoplasty specimens were frozen and then RNA was obtained following the microdissection method described above. Lesions were selected which were microlocalized and homogenous so that pure lesions could be obtained by 2 mm punches. Samples which had admixed normal epithelial, carcinoma-in-situ, or invasive cancer were not used for this study. Family history was obtained by chart review and/or interview to exclude familial breast cancer cases.

Nuclease Protection Assays. PCR primers were derived from BRCA1 sequence in GenBank (Accession number U14680); forward 5'CAA TTG GGC AGA TGT GT 3' (SEQ ID NO:50) and reverse 5'CTG GGG GAT CTG GGG TAT CA 3' (SEQ ID NO:51) which amplify a 113 bp region from exon 24, corresponding to bases 5587 to 5699 of the human BRCA1. This region was selected because this exon has not been reported to be differentially spliced unlike more 5' exons. The BRCA1 probe was cloned by subcloning this 113 bp band from normal human genomic DNA into PCR-scriptSK and screening for correct orientation. One ug of mRNA from each tissue sample was hybridized with 32P-labelled, T7 polymerase-generated RNA probes for BRCA1 and human glyceraldehyde-3-phosphate dehydrogenase (GADP) which would produce expected protected fragments of 113 and 140 respectively. The construction and use of the GADP probe for RNA standardization has been described above. The probe for ribonucleotide reductase M2 mRNA is the same as above and detects a 200 bp protected fragment.

Antisense oligonucleotide studies. Unmodified deoxyribonucleotide were analyzed by gel electrophoresis and UV shadowing and shown to be homogenous and of appropriate size. These oligonucleotide were purified by multiple lyophilization and solubilized in buffered media as described (Holt et al. 1988). Sequence of the unmodified antiBRCA1 oligonucleotide 5'AAG AGC AGA TAA ATC CAT 3'(SEQ ID NO: 52) and the complementary sense oligonucleotide 5'ATG GAT TTA TCT GCT CTT 3' (SEQ ID NO:53) correspond to the presumed translation initiation site at bases 12–137 of the GenBank sequence. The antisense oligonucleotide sequence was searched against GenBank and no significant homologies were identified to genes except BRCA1. Oligonucleotides were used according to our published methods (Holt et al. 1988). Primary mammary epithelial cells were cultured in serum-free medium supplemented with epidermal growth factor, insulin, hydrocortisone, ethanolamine, phosphorylethanolamine, and bovine pituitary extract. MCF-7 cells were cultured in Minimum Essential Medium Eagle (Modified) with Earle's salts and 2g/L sodium bicarbonate m supplemented with 2 mM L-glutamine, GMS-A (Gibco Cat. #680-1300AD), non-essential amino acids, and 2.5% fetal calf serum. Retinal pigmented perithelial cells were cultured in DMEM and 10% calf serum.

Our results indicate that the BRCA1 gene is expressed at higher levels in normal mammary cells than in breast cancer cells and that diminished expression of BRCA1 increased the proliferative rate of breast cells. This correlates well with the recent finding that patients with BRCA1 gene-linked hereditary breast cancer have tumors that grow more rapidly than comparable sporadic tumors (Marcus, J. et al. 1994). The decreased mRNA levels which were observed in sporadic breast cancers are not a consequence of differential splicing of the gene since the RNAs were quantitated with probes from the 3' end of the mRNA which is not a region where differential splicing is reported to occur (Miki, Y. et al 1994). Invasive sporadic cancers have BRCA1 mRNA levels which vary from 0 (in one case) to 20% of the levels observed in normal human mammary epithelium.

Examples 8 and 9 describe applications of the discovery of the function of the BRCA1 gene. Example 8 describes a gene therapy method and example 9 describes a drug screening method. The discovery of the diminished expression of the BRCA1 mRNA in breast cancer using the microdissection techniques of this invention provides an important scientific basis for these examples.

EXAMPLE 8

Gene Therapy Method Based on Determination of the Function of the BRCA1 Gene

Viral vectors containing a DNA sequence that codes for a protein having an amino acid sequence as essentially set forth in SEQ ID NO:49 can be constructed using techniques that are well known in the art. This sequence includes the BRCA1 gene product. Viral vectors containing a DNA sequence essentially as set forth in SEQ ID NO:47 (the BRCA1 gene) can be also constructed using techniques that are well known in the art. Retroviral vectors, adenoviral vectors, or adeno-associated viral vectors are all useful methods for delivering genes into breast cancer cells. An excellent candidate for use in breast cancer gene therapy is a Moloney-based retroviral vector with a breast selective MMTV promoter which we have reported previously (Wong et al). The viral vector is constructed by cloning the DNA sequence essentially as set forth in SEQ ID:47 into a retroviral vector such as a breast selective vector. Most preferably, the full-length (coding region) cDNA for BRCA1 is cloned into the retroviral vector. The retroviral vector would then be transfected into virus producing cells in the following manner: Viruses are prepared by transfecting PA317 cells with retroviral vector DNAs which were purified as described in Wong et al. Following transfection, the PA317 cells are split and then treated with G418 until individual clones can be identified and expanded. Each clone is then screened for its titer by analyzing its ability to transfer G418 resistance (since the retroviral vector contains a Neomycin resistance gene). The clones which have the highest titer are then frozen in numerous aliquots and tested for sterility, presence of replication-competent retrovirus, and presence of mycoplasm. The methods generally employed for construction and production of retroviral vectors have been described in Muller, 1990.

Once high titer viral vector producing clones have been identified, then patients with breast cancer can be treated by the following protocol: Viral vector expressing BRCA1 is infused into either solid tumors or infused into malignant effusions as a means for altering the growth of the tumor (since it is shown above that the BRCA1 gene product decreases the growth rate of breast cancer cells). Because viral vectors can efficiently transduce a high percentage of cancer cells, the tumors would be growth inhibited.

EXAMPLE 9

Method of Screening Compounds Capable of Activating Promoter Region of the BRCA1 Gene The discovery of the function of the BRCA1 gene provides a clear utility in that induction of expression of the gene and the resulting increase in level of protein encoded by the gene in the breast cancer cell should slow the proliferation of the breast cancer cells. Induction of expression of the gene can be caused by administering a compound to a patient that stimulates the regulatory regions of this gene, such as the promoter.

A method for screening compounds that activate the promoter of the BRCA1 gene is designed in the following way. A promoter sequence is a DNA segment that upregulates the expression of a gene. A sequence essentially as set forth in SEQ ID NO:48 can be ligated into a suitable vector, such as a plasmid, that contains a reporter gene using standard recombinant DNA techniques of restriction enzyme digests, ligation of fragment into vector, and transformation of bacteria. SEQ ID NO:48 includes the promoter sequence of the BRCA1 gene. A reporter gene is a gene that produces a readily detectable product. Examples of appropriate reporter genes which could be employed for this purpose include Beta-galactosidase or the chloramphenicol acetyltransferase gene.

The BRCA1 promoter/reporter gene combination can then be cloned into an expression vector or viral vector by standard recombinant DNA methods. Breast cancer cells can then be transfected with the expression vector containing the BRCA1 promoter/reporter gene using standard transfection methods which we have reported previously (Holt et al. PNAS 1986). A stable transformant with appropriate low level expression (breast cancer cells have low level BRCA1 expression as shown above) will be identified and then characterized to demonstrate proper DNA integration and expression. Methods of establishing and characterizing stable transformants have been described (Holt. MCB, 1994). Once an appropriate stable transformant cell line is identified, then we can plate the cell line in a manner than permits screening of hundreds or thousands of drugs or biological agents (for example in multiple 96 well microtiter plates). Level of expression of the reporter gene can be quantitated and agents which activate expression are thus identified. A positive result (i.e. induction of the promoter region) results in increased levels of the reporter gene resulting in either an increase in color (Beta-galactosidase assay) or specific radioactivity (Chloramphenicol acetyltransferase activity) through a reaction between the protein encoded by the reporter gene and a compound in the reaction medium. The compound produced by the reaction between the reporter gene protein and the compound in the reaction medium is the cause of the increase in color or specific radioactivity. These compounds can be called indicator compounds in that their presence indicates that the drug or biologial agent activitated the BRCA1 promoter. Methods for standardizing and performing Beta-galactosidase or chloramphenicol acetyltransferase assays have been reported (Holt et. al. MCB 1994). This method would be useful for initial screening of agents which increase BRCA1 expression. These agents could then be tested in more rigorous assays of breast cancer growth such as nude mouse tumor assays (Arteaga et al). This approach allows mass screening of large numbers of agents, sparing more rigorous animal tests for only promising compounds which score in the reporter gene assay described herein.

Thus, although there have been described particular embodiments of the present invention of a new and useful "Method for Detection and Treatment of Breast Cancer", it is not intended that such embodiments be construed as limitations upon the scope of this invention except as set forth in the following claims. It will be apparent to those skilled in the art that many changes and modifications may be made without departing from the invention in its broader aspects. For example, the above described techniques may be used in the diagnosis of other diseases and detection of differential genetic expression from microscopically-directed tissue samples of pathologic tissue. The production of a cDNA library produced as a result of the differential expression of genes in pathologic tissue in comparison to normal tissue provides the opportunity for further adiagnostic capabilities. Further, although there have been described certain experimental conditions used in the preferred embodiment, it is not intended that such conditions be construed as limitations upon the scope of this invention except as set forth in the following claims.

What is claimed is:

1. A method for suppressing the growth of a sporadic epithelial breast tumor in a mammal, the method comprising infusing directly to said sporadic tumor a vector comprising a BRCA1 nucleic acid sequence encoding a BRCA1 protein having tumor suppressor activity, the nucleic acid sequence operatively linked to a promoter, wherein production of the BRCA1 protein results in a decrease in the growth rate of said epithelial breast tumor.

2. A method for reducing the growth of a sporadic epithelial breast tumor in a mammal, comprising: infusing directly to said sporadic epithelial breast tumor a retroviral vector comprising BRCA1 DNA encoding a functionally active BRCA1 polypeptide operably linked to a promoter, wherein said BRCA1 polypeptide is expressed in said sporadic epithelial breast tumor at a level and for a period of time sufficient to reduce the growth of said sporadic epithelial breast tumor.

3. A method for reducing the growth of a sporadic epithelial breast tumor in a mammal, comprising: infusing directly to said sporadic epithelial breast tumor a viral vector comprising BRCA1 DNA encoding a functionally active BRCA1 polypeptide operably linked to a promoter, wherein said BRCA1 polypeptide is expressed in said sporadic epithelial breast tumor at a level and for a period of time sufficient to reduce the growth of said sporadic epithelial breast tumor.

4. The method of claim 3, wherein the viral vector is an adenoviral vector.

* * * * *

SEQUENCE LISTING

<160> NUMBER OF SEQ ID NOS: 61

<210> SEQ ID NO 1
<211> LENGTH: 264
<212> TYPE: DNA
<213> ORGANISM: Homo sapiens

<400> SEQUENCE: 1

```
ttgggaattg ggtacgcggg ccccccactg tgccgaattc ctgcatgcgg gggatccact    60
agttcagagc aggccgccac ccgtaggact ccagcttttg ttcgttccct ttagtgaggg   120
ttaattttcg agcttggcgt aatcatggtc atagctgttt cctgtgtgaa attgttatcc   180
gctcacaatt ccacacaaca tacgagccgg aagcataaaa gtgtaaagcc tggggtgcct   240
aatgagtgag ctaactcaca ttaa                                          264
```

<210> SEQ ID NO 2
<211> LENGTH: 73
<212> TYPE: DNA
<213> ORGANISM: Homo sapiens

<400> SEQUENCE: 2

```
tagcccggtt atcgaaatag ccacagcgcc tcttcactat cagcagtacg ccgcccagtt    60
gtacggacac gga                                                      73
```

<210> SEQ ID NO 3
<211> LENGTH: 46
<212> TYPE: DNA
<213> ORGANISM: Homo sapiens

<400> SEQUENCE: 3

```
tgcccgatgt gtgtcgtaca actggcgctg tggctgattt cgataa                   46
```

<210> SEQ ID NO 4
<211> LENGTH: 72
<212> TYPE: DNA

<213> ORGANISM: Homo sapiens
<220> FEATURE:
<221> NAME/KEY: misc_feature
<222> LOCATION: (53)..(57)
<223> OTHER INFORMATION: n=a, g, c, or t/u

<400> SEQUENCE: 4
tagcccatga gttcgtgtcc gtacaactgg ggcgctgtgg ctgatttcga tannnnnagc    60
atcagcccga cg    72

<210> SEQ ID NO 5
<211> LENGTH: 84
<212> TYPE: DNA
<213> ORGANISM: Homo sapiens

<400> SEQUENCE: 5
tagcccggtt atcgaaatca gccacagcgc ctaacttctg cagaagcctt tgaccatcac    60
cagttgtacg gacacgaact catc    84

<210> SEQ ID NO 6
<211> LENGTH: 99
<212> TYPE: DNA
<213> ORGANISM: Homo sapiens

<400> SEQUENCE: 6
gtggtttccg aaattcctgg gaaggggggt gctggcgtgt ggaattgtcg cggcccctgg    60
tctgccgcgg cgttttttgt ctacattcgt cgtagctcg    99

<210> SEQ ID NO 7
<211> LENGTH: 88
<212> TYPE: DNA
<213> ORGANISM: Homo sapiens

<400> SEQUENCE: 7
atcagcgcgc gacattcggg tacccgcgcc ccccctccg tcggaattcc tcgagccggg    60
atccatagga tgtggagtta gttttgtt    88

<210> SEQ ID NO 8
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 8
cgcgacggcc gcgcgtctgc caggg    25

<210> SEQ ID NO 9
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 9
cgcccctgcg ttaccctccc cgccg    25

<210> SEQ ID NO 10
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 10
ggatggcgtc ctgtaacccg acgct          25

<210> SEQ ID NO 11
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 11
actgggctgt cctgcggtgg cgggg          25

<210> SEQ ID NO 12
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 12
ctgagaggta gccgcgcgga ggctg          25

<210> SEQ ID NO 13
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 13
gcctggccgc gacacggatt accgc          25

<210> SEQ ID NO 14
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 14
ttagcgcatg gtggacctgg agacg          25

<210> SEQ ID NO 15
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 15
tgtggttacg tcagcgaagg taata          25

<210> SEQ ID NO 16
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 16
agtcgcacgc atgtcacgct ccgcc          25

<210> SEQ ID NO 17

<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 17
tatccaagcg gcaggctacg aggcc                                  25

<210> SEQ ID NO 18
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 18
ggcgcgcccg acggtctggt atcta                                  25

<210> SEQ ID NO 19
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 19
ctccctcccc ggactcgggg ttagt                                  25

<210> SEQ ID NO 20
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 20
atgcgggcgg ctcgggcctg gtcgc                                  25

<210> SEQ ID NO 21
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 21
cgtgaagcct atgccctccc tcaac                                  25

<210> SEQ ID NO 22
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 22
gtgccgtcgt agcccttcag cgatc                                  25

<210> SEQ ID NO 23
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 23
gcgacactag gctcccggag gaggg                                                25

<210> SEQ ID NO 24
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 24
tgggccaggc ctccgggccc ggtat                                                25

<210> SEQ ID NO 25
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 25
ccggaactgc gatagcgtcc gtccc                                                25

<210> SEQ ID NO 26
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 26
agcggacacc tgtttcccga gagcc                                                25

<210> SEQ ID NO 27
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 27
aacgggtgga catccgcctg ccgcc                                                25

<210> SEQ ID NO 28
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 28
tgaaccacga tgtcaatcgt cccga                                                25

<210> SEQ ID NO 29
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 29
tcatccccgc cgaaagacgc tcgcc                                                25

<210> SEQ ID NO 30
<211> LENGTH: 25
<212> TYPE: DNA

<210> SEQ ID NO 30
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 30
ataggctgcg gcacgcgctg ggact                                    25

<210> SEQ ID NO 31
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 31
gaccaggtgc gcacgagcat gtaca                                    25

<210> SEQ ID NO 32
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 32
agcgtagtca tcggccttcg cgccc                                    25

<210> SEQ ID NO 33
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 33
ggcccctagc ccagggtgaa gccca                                    25

<210> SEQ ID NO 34
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 34
cccagtgcta cgggccgccc caagc                                    25

<210> SEQ ID NO 35
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 35
ccttcctggg ttacctgccc tcggg                                    25

<210> SEQ ID NO 36
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 36
tccggacagc agccacgcca agggc                                    25

<210> SEQ ID NO 37
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 37
acgcgctggt ccaccgaggc ctgat                                    25

<210> SEQ ID NO 38
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 38
cgatgcaagg ccagcagcac tcgac                                    25

<210> SEQ ID NO 39
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 39
cccccggagc ggaccaccgg acgtg                                    25

<210> SEQ ID NO 40
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 40
agcggggagg gatcggggc caagc                                     25

<210> SEQ ID NO 41
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 41
gcctggtgta ggcaggcagc tctta                                    25

<210> SEQ ID NO 42
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 42 ccaccoctgt agtgcgggct gcgag                                    25

<210> SEQ ID NO 43
<211> LENGTH: 25
<212> TYPE: DNA
<213> ORGANISM: Artificial Sequence
<220> FEATURE:

<223> OTHER INFORMATION: Synthesized PCR Primer

<400> SEQUENCE: 43
ggaacccgac gcccgtccag ggttc                                         25

<210> SEQ ID NO 44
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 44
tcgggcagca aggccgggac gctcc                                         25

<210> SEQ ID NO 45
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 45
gacgggggac gggctaggtg gctta                                         25

<210> SEQ ID NO 46
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 46
cttgttgccg gcggagaggg ctgcc                                         25

<210> SEQ ID NO 47
<211> LENGTH: 5712
<212> TYPE: DNA
<213> ORGANISM: Homo sapiens
<220> FEATURE:
<221> NAME/KEY: CDS
<222> LOCATION: (120)..(5708)
<221> NAME/KEY: misc_feature
<222> LOCATION: (4532)..(4535)
<223> OTHER INFORMATION: Xaa=any amino acid

<400> SEQUENCE: 47
agctcgctga gacttcctgg accccgcacc aggctgtggg gtttctcaga taactgggcc      60
cctgcgctca ggaggccttc accctctgct ctgggtaaag ttcattggaa cagaaagaa      119 atg gat tta tct gct ctt cgc gtt gaa gaa gta caa aat gtc att aat      167
Met Asp Leu Ser Ala Leu Arg Val Glu Glu Val Gln Asn Val Ile Asn
1               5                  10                  15 gct atg cag aaa atc tta gag tgt ccc atc tgt ctg gag ttg atc aag      215
Ala Met Gln Lys Ile Leu Glu Cys Pro Ile Cys Leu Glu Leu Ile Lys
            20                  25                  30 gaa cct gtc tcc aca aag tgt gac cac ata ttt tgc aaa ttt tgc atg      263
Glu Pro Val Ser Thr Lys Cys Asp His Ile Phe Cys Lys Phe Cys Met
        35                  40                  45 ctg aaa ctt ctc aac cag aag aaa ggg cct tca cag tgt cct tta tgt      311
Leu Lys Leu Leu Asn Gln Lys Lys Gly Pro Ser Gln Cys Pro Leu Cys
    50                  55                  60 aag aat gat ata acc aaa agg agc cta caa gaa agt acg aga ttt agt      359
Lys Asn Asp Ile Thr Lys Arg Ser Leu Gln Glu Ser Thr Arg Phe Ser
65                  70                  75                  80

```
caa ctt gtt gaa gag cta ttg aaa atc att tgt gct ttt cag ctt gac    407
Gln Leu Val Glu Glu Leu Leu Lys Ile Ile Cys Ala Phe Gln Leu Asp
             85                  90                  95 aca ggt ttg gag tat gca aac agc tat aat ttt gca aaa aag gaa aat    455
Thr Gly Leu Glu Tyr Ala Asn Ser Tyr Asn Phe Ala Lys Lys Glu Asn
            100                 105                 110 aac tct cct gaa cat cta aaa gat gaa gtt tct atc atc caa agt atg    503
Asn Ser Pro Glu His Leu Lys Asp Glu Val Ser Ile Ile Gln Ser Met
        115                 120                 125 ggc tac aga aac cgt gcc aaa aga ctt cta cag agt gaa ccc gaa aat    551
Gly Tyr Arg Asn Arg Ala Lys Arg Leu Leu Gln Ser Glu Pro Glu Asn
    130                 135                 140 cct tcc ttg cag gaa acc agt ctc agt gtc caa ctc tct aac ctt gga    599
Pro Ser Leu Gln Glu Thr Ser Leu Ser Val Gln Leu Ser Asn Leu Gly
145                 150                 155                 160 act gtg aga act ctg agg aca aag cag cgg ata caa cct caa aag acg    647
Thr Val Arg Thr Leu Arg Thr Lys Gln Arg Ile Gln Pro Gln Lys Thr
                165                 170                 175 tct gtc tac att gaa ttg gga tct gat tct tct gaa gat acc gtt aat    695
Ser Val Tyr Ile Glu Leu Gly Ser Asp Ser Ser Glu Asp Thr Val Asn
            180                 185                 190 aag gca act tat tgc agt gtg gga gat caa gaa ttg tta caa atc acc    743
Lys Ala Thr Tyr Cys Ser Val Gly Asp Gln Glu Leu Leu Gln Ile Thr
        195                 200                 205 cct caa gga acc agg gat gaa atc agt ttg gat tct gca aaa aag gct    791
Pro Gln Gly Thr Arg Asp Glu Ile Ser Leu Asp Ser Ala Lys Lys Ala
    210                 215                 220 gct tgt gaa ttt tct gag acg gat gta aca aat act gaa cat cat caa    839
Ala Cys Glu Phe Ser Glu Thr Asp Val Thr Asn Thr Glu His His Gln
225                 230                 235                 240 ccc agt aat aat gat ttg aac acc act gag aag cgt gca gct gag agg    887
Pro Ser Asn Asn Asp Leu Asn Thr Thr Glu Lys Arg Ala Ala Glu Arg
                245                 250                 255 cat cca gaa aag tat cag ggt agt tct gtt tca aac ttg cat gtg gag    935
His Pro Glu Lys Tyr Gln Gly Ser Ser Val Ser Asn Leu His Val Glu
            260                 265                 270 cca tgt ggc aca aat act cat gcc agc tca tta cag cat gag aac agc    983
Pro Cys Gly Thr Asn Thr His Ala Ser Ser Leu Gln His Glu Asn Ser
        275                 280                 285 agt tta tta ctc act aaa gac aga atg aat gta gaa aag gct gaa ttc   1031
Ser Leu Leu Leu Thr Lys Asp Arg Met Asn Val Glu Lys Ala Glu Phe
    290                 295                 300 tgt aat aaa agc aaa cag cct ggc tta gca agg agc caa cat aac aga   1079
Cys Asn Lys Ser Lys Gln Pro Gly Leu Ala Arg Ser Gln His Asn Arg
305                 310                 315                 320 tgg gct gga agt aag gaa aca tgt aat gat agg cgg act ccc agc aca   1127
Trp Ala Gly Ser Lys Glu Thr Cys Asn Asp Arg Arg Thr Pro Ser Thr
                325                 330                 335 gaa aaa aag gta gat ctg aat gct gat ccc ctg tgt gag aga aaa gaa   1175
Glu Lys Lys Val Asp Leu Asn Ala Asp Pro Leu Cys Glu Arg Lys Glu
            340                 345                 350 tgg aat aag cag aaa ctg cca tgc tca gag aat cct aga gat act gaa   1223
Trp Asn Lys Gln Lys Leu Pro Cys Ser Glu Asn Pro Arg Asp Thr Glu
        355                 360                 365 gat gtt cct tgg ata aca cta aat agc agc att cag aaa gtt aat gag   1271
Asp Val Pro Trp Ile Thr Leu Asn Ser Ser Ile Gln Lys Val Asn Glu
    370                 375                 380 tgg ttt tcc aga agt gat gaa ctg tta ggt tct gat gac tca cat gat   1319
Trp Phe Ser Arg Ser Asp Glu Leu Leu Gly Ser Asp Asp Ser His Asp
```

-continued

| | | | | | | | | | | | | | | | | |
|---|---|---|---|---|---|---|---|---|---|---|---|---|---|---|---|---|
| 385 | | | | | 390 | | | | | 395 | | | | | 400 | |

```
ggg gag tct gaa tca aat gcc aaa gta gct gat gta ttg gac gtt cta      1367
Gly Glu Ser Glu Ser Asn Ala Lys Val Ala Asp Val Leu Asp Val Leu
            405                 410                 415 aat gag gta gat gaa tat tct ggt tct tca gag aaa ata gac tta ctg      1415
Asn Glu Val Asp Glu Tyr Ser Gly Ser Ser Glu Lys Ile Asp Leu Leu
                420                 425                 430 gcc agt gat cct cat gag gct tta ata tgt aaa agt gaa aga gtt cac      1463
Ala Ser Asp Pro His Glu Ala Leu Ile Cys Lys Ser Asp Arg Val His
            435                 440                 445 tcc aaa tca gta gag agt aat att gaa gac aaa ata ttt ggg aaa acc      1511
Ser Lys Ser Val Glu Ser Asn Ile Glu Asp Lys Ile Phe Gly Lys Thr
        450                 455                 460 tat cgg aag aag gca agc ctc ccc aac tta agc cat gta act gaa aat      1559
Tyr Arg Lys Lys Ala Ser Leu Pro Asn Leu Ser His Val Thr Glu Asn
465                 470                 475                 480 cta att ata gga gca ttt gtt act gag cca cag ata ata caa gag cgt      1607
Leu Ile Ile Gly Ala Phe Val Thr Glu Pro Gln Ile Ile Gln Glu Arg
                485                 490                 495 ccc ctc aca aat aaa tta aag cgt aaa agg aga cct aca tca ggc ctt      1655
Pro Leu Thr Asn Lys Leu Lys Arg Lys Arg Arg Pro Thr Ser Gly Leu
            500                 505                 510 cat cct gag gat ttt atc aag aaa gca gat ttg gca gtt caa aag act      1703
His Pro Glu Asp Phe Ile Lys Lys Ala Asp Leu Ala Val Gln Lys Thr
            515                 520                 525 cct gaa atg ata aat cag gga act aac caa acg gag cag aat ggt caa      1751
Pro Glu Met Ile Asn Gln Gly Thr Asn Gln Thr Glu Gln Asn Gly Gln
        530                 535                 540 gtg atg aat att act aat agt ggt cat gag aat aaa aca aaa ggt gat      1799
Val Met Asn Ile Thr Asn Ser Gly His Glu Asn Lys Thr Lys Gly Asp
545                 550                 555                 560 tct att cag aat gag aaa aat cct aac cca ata gaa tca ctc gaa aaa      1847
Ser Ile Gln Asn Glu Lys Asn Pro Asn Pro Ile Glu Ser Leu Glu Lys
                565                 570                 575 gaa tct gct ttc aaa acg aaa gct gaa cct ata agc agc agt ata agc      1895
Glu Ser Ala Phe Lys Thr Lys Ala Glu Pro Ile Ser Ser Ser Ile Ser
            580                 585                 590 aat atg gaa ctc gaa tta aat atc cac aat tca aaa gca cct aaa aag      1943
Asn Met Glu Leu Glu Leu Asn Ile His Asn Ser Lys Ala Pro Lys Lys
            595                 600                 605 aat agg ctg agg agg aag tct tct acc agg cat att cat gcg ctt gaa      1991
Asn Arg Leu Arg Arg Lys Ser Ser Thr Arg His Ile His Ala Leu Glu
        610                 615                 620 cta gta gtc agt aga aat cta agc cca cct aat tgt act gaa ttg caa      2039
Leu Val Val Ser Arg Asn Leu Ser Pro Pro Asn Cys Thr Glu Leu Gln
625                 630                 635                 640 att gat agt tgt tct agc agt gaa gag ata aag aaa aaa aag tac aac      2087
Ile Asp Ser Cys Ser Ser Ser Glu Glu Ile Lys Lys Lys Lys Tyr Asn
                645                 650                 655 caa atg cca gtc agg cac agc aga aac cta caa ctc atg gaa ggt aaa      2135
Gln Met Pro Val Arg His Ser Arg Asn Leu Gln Leu Met Glu Gly Lys
            660                 665                 670 gaa cct gca act gga gcc aag aag agt aac aag cca aat gaa cag aca      2183
Glu Pro Ala Thr Gly Ala Lys Lys Ser Asn Lys Pro Asn Glu Gln Thr
            675                 680                 685 agt aaa aga cat gac agc gat act ttc cca gag ctg aag tta aca aat      2231
Ser Lys Arg His Asp Ser Asp Thr Phe Pro Glu Leu Lys Leu Thr Asn
        690                 695                 700 gca cct ggt tct ttt act aag tgt tca aat acc agt gaa ctt aaa gaa      2279
Ala Pro Gly Ser Phe Thr Lys Cys Ser Asn Thr Ser Glu Leu Lys Glu
```

```
Ala Pro Gly Ser Phe Thr Lys Cys Ser Asn Thr Ser Glu Leu Lys Glu
705                 710                 715                 720 ttt gtc aat cct agc ctt cca aga gaa gaa aaa gaa gag aaa cta gaa      2327
Phe Val Asn Pro Ser Leu Pro Arg Glu Glu Lys Glu Glu Lys Leu Glu
                725                 730                 735 aca gtt aaa gtg tct aat aat gct gaa gac ccc aaa gat ctc atg tta      2375
Thr Val Lys Val Ser Asn Asn Ala Glu Asp Pro Lys Asp Leu Met Leu
            740                 745                 750 agt gga gaa agg gtt ttg caa act gaa aga tct gta gag agt agc agt      2423
Ser Gly Glu Arg Val Leu Gln Thr Glu Arg Ser Val Glu Ser Ser Ser
        755                 760                 765 att tca ttg gta cct ggt act gat tat ggc act cag gaa agt atc tcg      2471
Ile Ser Leu Val Pro Gly Thr Asp Tyr Gly Thr Gln Glu Ser Ile Ser
    770                 775                 780 tta ctg gaa gtt agc act cta ggg aag gca aaa aca gaa cca aat aaa      2519
Leu Leu Glu Val Ser Thr Leu Gly Lys Ala Lys Thr Glu Pro Asn Lys
785                 790                 795                 800 tgt gtg agt cag tgt gca gca ttt gaa aac ccc aag gga cta att cat      2567
Cys Val Ser Gln Cys Ala Ala Phe Glu Asn Pro Lys Gly Leu Ile His
                805                 810                 815 ggt tgt tcc aaa gat aat aga aat gac aca gaa ggc ttt aag tat cca      2615
Gly Cys Ser Lys Asp Asn Arg Asn Asp Thr Glu Gly Phe Lys Tyr Pro
            820                 825                 830 ttg gga cat gaa gtt aac cac agt cgg gaa aca agc ata gaa atg gaa      2663
Leu Gly His Glu Val Asn His Ser Arg Glu Thr Ser Ile Glu Met Glu
        835                 840                 845 gaa agt gaa ctt gat gct cag tat ttg cag aat aca ttc aag gtt tca      2711
Glu Ser Glu Leu Asp Ala Gln Tyr Leu Gln Asn Thr Phe Lys Val Ser
    850                 855                 860 aag cgc cag tca ttt gct ccg ttt tca aat cca gga aat gca gaa gag      2759
Lys Arg Gln Ser Phe Ala Pro Phe Ser Asn Pro Gly Asn Ala Glu Glu
865                 870                 875                 880 gaa tgt gca aca ttc tct gcc cac tct ggg tcc tta aag aaa caa agt      2807
Glu Cys Ala Thr Phe Ser Ala His Ser Gly Ser Leu Lys Lys Gln Ser
                885                 890                 895 cca aaa gtc act ttt gaa tgt gaa caa aag gaa gaa aat caa gga aag      2855
Pro Lys Val Thr Phe Glu Cys Glu Gln Lys Glu Glu Asn Gln Gly Lys
            900                 905                 910 aat gag tct aat atc aag cct gta cag aca gtt aat atc act gca ggc      2903
Asn Glu Ser Asn Ile Lys Pro Val Gln Thr Val Asn Ile Thr Ala Gly
        915                 920                 925 ttt cct gtg gtt ggt cag aaa gat aag cca gtt gat aat gcc aaa tgt      2951
Phe Pro Val Val Gly Gln Lys Asp Lys Pro Val Asp Asn Ala Lys Cys
    930                 935                 940 agt atc aaa gga ggc tct agg ttt tgt cta tca tct cag ttc aga ggc      2999
Ser Ile Lys Gly Gly Ser Arg Phe Cys Leu Ser Ser Gln Phe Arg Gly
945                 950                 955                 960 aac gaa act gga ctc att act cca aat aaa cat gga ctt tta caa aac      3047
Asn Glu Thr Gly Leu Ile Thr Pro Asn Lys His Gly Leu Leu Gln Asn
                965                 970                 975 cca tat cgt ata cca cca ctt ttt ccc atc aag tca ttt gtt aaa act      3095
Pro Tyr Arg Ile Pro Pro Leu Phe Pro Ile Lys Ser Phe Val Lys Thr
            980                 985                 990 aaa tgt aag aaa aat ctg cta gag gaa aac ttt gag gaa cat tca atg      3143
Lys Cys Lys Lys Asn Leu Leu Glu Glu Asn Phe Glu Glu His Ser Met
        995                 1000                1005 tca cct gaa aga gaa atg gga aat gag aac att cca agt aca gtg agc      3191
Ser Pro Glu Arg Glu Met Gly Asn Glu Asn Ile Pro Ser Thr Val Ser
    1010                1015                1020
```

```
aca att agc cgt aat aac att aga gaa aat gtt ttt aaa gaa gcc agc      3239
Thr Ile Ser Arg Asn Asn Ile Arg Glu Asn Val Phe Lys Glu Ala Ser
1025                1030                1035                1040 tca agc aat att aat gaa gta ggt tcc agt act aat gaa gtg ggc tcc      3287
Ser Ser Asn Ile Asn Glu Val Gly Ser Ser Thr Asn Glu Val Gly Ser
                1045                1050                1055 agt att aat gaa ata ggt tcc agt gat gaa aac att caa gca gaa cta      3335
Ser Ile Asn Glu Ile Gly Ser Ser Asp Glu Asn Ile Gln Ala Glu Leu
                1060                1065                1070 ggt aga aac aga ggg cca aaa ttg aat gct atg ctt aga tta ggg gtt      3383
Gly Arg Asn Arg Gly Pro Lys Leu Asn Ala Met Leu Arg Leu Gly Val
            1075                1080                1085 ttg caa cct gag gtc tat aaa caa agt ctt cct gga agt aat tgt aag      3431
Leu Gln Pro Glu Val Tyr Lys Gln Ser Leu Pro Gly Ser Asn Cys Lys
        1090                1095                1100 cat cct gaa ata aaa aag caa gaa tat gaa gaa gta gtt cag act gtt      3479
His Pro Glu Ile Lys Lys Gln Glu Tyr Glu Glu Val Val Gln Thr Val
1105                1110                1115                1120 aat aca gat ttc tct cca tat ctg att tca gat aac tta gaa cag cct      3527
Asn Thr Asp Phe Ser Pro Tyr Leu Ile Ser Asp Asn Leu Glu Gln Pro
                1125                1130                1135 atg gga agt agt cat gca tct cag gtt tgt tct gag aca cct gat gac      3575
Met Gly Ser Ser His Ala Ser Gln Val Cys Ser Glu Thr Pro Asp Asp
                1140                1145                1150 ctg tta gat gat ggt gaa ata aag gaa gat act agt ttt gct gaa aat      3623
Leu Leu Asp Asp Gly Glu Ile Lys Glu Asp Thr Ser Phe Ala Glu Asn
            1155                1160                1165 gac att aag gaa agt tct gct gtt ttt agc aaa agc gtc cag aaa gga      3671
Asp Ile Lys Glu Ser Ser Ala Val Phe Ser Lys Ser Val Gln Lys Gly
        1170                1175                1180 gag ctt agc agg agt cct agc cct ttc acc cat aca cat ttg gct cag      3719
Glu Leu Ser Arg Ser Pro Ser Pro Phe Thr His Thr His Leu Ala Gln
1185                1190                1195                1200 ggt tac cga aga ggg gcc aag aaa tta gag tcc tca gaa gag aac tta      3767
Gly Tyr Arg Arg Gly Ala Lys Lys Leu Glu Ser Ser Glu Glu Asn Leu
                1205                1210                1215 tct agt gag gat gaa gag ctt ccc tgc ttc caa cac ttg tta ttt ggt      3815
Ser Ser Glu Asp Glu Glu Leu Pro Cys Phe Gln His Leu Leu Phe Gly
                1220                1225                1230 aaa gta aac aat ata cct tct cag tct act agg cat agc acc gtt gct      3863
Lys Val Asn Asn Ile Pro Ser Gln Ser Thr Arg His Ser Thr Val Ala
            1235                1240                1245 acc gag tgt ctg tct aag aac aca gag gag aat tta tta tca ttg aag      3911
Thr Glu Cys Leu Ser Lys Asn Thr Glu Glu Asn Leu Leu Ser Leu Lys
        1250                1255                1260 aat agc tta aat gac tgc agt aac cag gta ata ttg gca aag gca tct      3959
Asn Ser Leu Asn Asp Cys Ser Asn Gln Val Ile Leu Ala Lys Ala Ser
1265                1270                1275                1280 cag gaa cat cac ctt agt gag gaa aca aaa tgt tct gct agc ttg ttt      4007
Gln Glu His His Leu Ser Glu Glu Thr Lys Cys Ser Ala Ser Leu Phe
                1285                1290                1295 tct tca cag tgc agt gaa ttg gaa gac ttg act gca aat aca aac acc      4055
Ser Ser Gln Cys Ser Glu Leu Glu Asp Leu Thr Ala Asn Thr Asn Thr
                1300                1305                1310 cag gat cct ttc ttg att ggt tct tcc aaa caa atg agg cat cag tct      4103
Gln Asp Pro Phe Leu Ile Gly Ser Ser Lys Gln Met Arg His Gln Ser
            1315                1320                1325 gaa agc cag gga gtt ggt ctg agt gac aag gaa ttg gtt tca gat gat      4151
Glu Ser Gln Gly Val Gly Leu Ser Asp Lys Glu Leu Val Ser Asp Asp
        1330                1335                1340
```

-continued

| | |
|---|---|
| gaa gaa aga gga acg ggc ttg gaa gaa aat aat caa gaa gag caa agc<br>Glu Glu Arg Gly Thr Gly Leu Glu Glu Asn Asn Gln Glu Glu Gln Ser<br>1345                      1350                1355                      1360 | 4199 |
| atg gat tca aac tta ggt gaa gca gca tct ggg tgt gag agt gaa aca<br>Met Asp Ser Asn Leu Gly Glu Ala Ala Ser Gly Cys Glu Ser Glu Thr<br>                        1365                      1370                      1375 | 4247 |
| agc gtc tct gaa gac tgc tca ggg cta tcc tct cag agt gac att tta<br>Ser Val Ser Glu Asp Cys Ser Gly Leu Ser Ser Gln Ser Asp Ile Leu<br>           1380                      1385                      1390 | 4295 |
| acc act cag cag agg gat acc atg caa cat aac ctg ata aag ctc cag<br>Thr Thr Gln Gln Arg Asp Thr Met Gln His Asn Leu Ile Lys Leu Gln<br>1395                      1400                      1405 | 4343 |
| cag gaa atg gct gaa cta gaa gct gtg tta gaa cag cat ggg agc cag<br>Gln Glu Met Ala Glu Leu Glu Ala Val Leu Glu Gln His Gly Ser Gln<br>          1410                      1415                      1420 | 4391 |
| cct tct aac agc tac cct tcc atc ata agt gac tct tct gcc ctt gag<br>Pro Ser Asn Ser Tyr Pro Ser Ile Ile Ser Asp Ser Ser Ala Leu Glu<br>1425                      1430                      1435                      1440 | 4439 |
| gac ctg cga aat cca gaa caa agc aca tca gaa aaa gca gta tta act<br>Asp Leu Arg Asn Pro Glu Gln Ser Thr Ser Glu Lys Val Leu Gln Thr<br>                        1445                      1450                      1455 | 4487 |
| tca cag aaa agt agt gaa tac cct ata agc cag aat cca gaa ggc ctt<br>Ser Gln Lys Ser Ser Glu Tyr Pro Ile Ser Gln Asn Pro Glu Gly Xaa<br>          1460                      1465                      1470 | 4535 |
| tct gct gac aag ttt gag gtg tct gca gat agt tct acc agt aaa aat<br>Ser Ala Asp Lys Phe Glu Val Ser Ala Asp Ser Ser Thr Ser Lys Asn<br>1475                      1480                      1485 | 4583 |
| aaa gaa cca gga gtg gaa agg tca tcc cct tct aaa tgc cca tca tta<br>Lys Glu Pro Gly Val Glu Arg Ser Ser Pro Ser Lys Cys Pro Ser Leu<br>          1490                      1495                      1500 | 4631 |
| gat gat agg tgg tac atg cac agt tgc tct ggg agt ctt cag aat aga<br>Asp Asp Arg Trp Tyr Met His Ser Cys Ser Gly Ser Leu Gln Asn Arg<br>1505                      1510                      1515                      1520 | 4679 |
| aac tac cca tct caa gag gag ctc att aag gtt gtt gat gtg gag gag<br>Asn Tyr Pro Pro Gln Glu Glu Leu Ile Lys Val Val Asp Val Glu Glu<br>                        1525                      1530                      1535 | 4727 |
| caa cag ctg gaa gag tct ggg cca cac gat ttg acg gaa aca tct tac<br>Gln Gln Leu Glu Glu Ser Gly Pro His Asp Leu Thr Glu Thr Ser Tyr<br>          1540                      1545                      1550 | 4775 |
| ttg cca agg caa gat cta gag gga acc cct tac ctg gaa tct gga atc<br>Leu Pro Arg Gln Asp Leu Glu Gly Thr Pro Tyr Leu Glu Ser Gly Ile<br>1555                      1560                      1565 | 4823 |
| agc ctc ttc tct gat gac cct gaa tct gat cct tct gaa gac aga gcc<br>Ser Leu Phe Ser Asp Asp Pro Glu Ser Asp Pro Ser Glu Asp Arg Ala<br>          1570                      1575                      1580 | 4871 |
| cca gag tca gct cgt gtt ggc aac ata cca tct tca acc tct gca ttg<br>Pro Glu Ser Ala Arg Val Gly Asn Ile Pro Ser Ser Thr Ser Ala Leu<br>1585                      1590                      1595                      1600 | 4919 |
| aaa gtt ccc caa ttg aaa gtt gca gaa tct gcc cag agt cca gct gct<br>Lys Val Pro Gln Leu Lys Val Ala Glu Ser Ala Gln Ser Pro Ala Ala<br>                        1605                      1610                      1615 | 4967 |
| gct cat act act gat act gct ggg tat aat gca atg gaa gaa agt gtg<br>Ala His Thr Thr Asp Thr Ala Gly Tyr Asn Ala Met Glu Glu Ser Val<br>                        1620                      1625                      1630 | 5015 |
| agc agg gag aag cca gaa ttg aca gct tca aca gaa agg gtc aac aaa<br>Ser Arg Glu Lys Pro Glu Leu Thr Ala Ser Thr Glu Arg Val Asn Lys<br>          1635                      1640                      1645 | 5063 |
| aga atg tcc atg gtg gtg tct ggc ctg acc cca gaa gaa ttt atg ctc<br>Arg Met Ser Met Val Val Ser Gly Leu Thr Pro Glu Glu Phe Met Leu | 5111 |

-continued

```
        1650                1655                1660
gtg tac aag ttt gcc aga aaa cac cac atc act tta act aat cta att      5159
Val Tyr Lys Phe Ala Arg Lys His His Ile Thr Leu Thr Asn Leu Ile
1665                1670                1675                1680 act gaa gag act act cat gtt gtt atg aaa aca gat gct gag ttt gtg      5207
Thr Glu Glu Thr Thr His Val Val Met Lys Thr Asp Ala Glu Phe Val
                    1685                1690                1695 tgt gaa cgg aca ctg aaa tat ttt cta gga att gcg gga gga aaa tgg      5255
Cys Glu Arg Thr Leu Lys Tyr Phe Leu Gly Ile Ala Gly Gly Lys Trp
            1700                1705                1710 gta gtt agc tat ttc tgg gtg acc cag tct att aaa gaa aga aaa atg      5303
Val Val Ser Tyr Phe Trp Val Thr Gln Ser Ile Lys Glu Arg Lys Met
        1715                1720                1725 ctg aat gag cat gat ttt gaa gtc aga gga gat gtg gtc aat gga aga      5351
Leu Asn Glu His Asp Phe Glu Val Arg Gly Asp Val Val Asn Gly Arg
    1730                1735                1740 aac cac caa ggt cca aag cga gca aga gaa tcc cag gac aga aag atc      5399
Asn His Gln Gly Pro Lys Arg Ala Arg Glu Ser Gln Asp Arg Lys Ile
1745                1750                1755                1760 ttc agg ggg cta gaa atc tgt tgc tat ggg ccc ttc acc aac atg ccc      5447
Phe Arg Gly Leu Glu Ile Cys Cys Tyr Gly Pro Phe Thr Asn Met Pro
                    1765                1770                1775 aca gat caa ctg gaa tgg atg gta cag ctg tgt ggt gct tct gtg gtg      5495
Thr Asp Gln Leu Glu Trp Met Val Gln Leu Cys Gly Ala Ser Val Val
            1780                1785                1790 aag gag ctt tca tca ttc acc ctt ggc aca ggt gtc cac cca att gtg      5543
Lys Glu Leu Ser Ser Phe Thr Leu Gly Thr Gly Val His Pro Ile Val
        1795                1800                1805 gtt gtg cag cca gat gcc tgg aca gag gac aat ggc ttc cat gca att      5591
Val Val Gln Pro Asp Ala Trp Thr Glu Asp Asn Gly Phe His Ala Ile
    1810                1815                1820 ggg cag atg tgt gag gca cct gtg gtg acc cga gag tgg gtg ttg gac      5639
Gly Gln Met Cys Glu Ala Pro Val Val Thr Arg Glu Trp Val Leu Asp
1825                1830                1835                1840 agt gta gca ctc tac cag tgc cag gag ctg gac acc tac ctg ata ccc      5687
Ser Val Ala Leu Tyr Gln Cys Gln Glu Leu Asp Thr Tyr Leu Ile Pro
                    1845                1850                1855 cag atc ccc cac agc cac tac tgat                                     5712
Gln Ile Pro His Ser His Tyr
            1860

<210> SEQ ID NO 48
<211> LENGTH: 1237
<212> TYPE: DNA
<213> ORGANISM: Homo sapiens

<400> SEQUENCE: 48
ttccgggact ctactacctt tacccagacg agagggtgaa ggcctcctga tcgcaggggc      60
ccagttatct gagaaacccc acagcctggt gcggggtcca ggaagtctca gcgagctcac     120
gccgcgcagt cgcagtttta atttatctgt aattcccgcg cttttccgtt gccacggaaa     180
ccaaggggct accgctaagc agcagcctct cagaatacga aatcaaggta caatcagagg     240
aagggaggga cagaaagagc caagcgtctc tcggggctct ggattggcca cccagtctgc     300
ccccggatga cgtaaaagga aagagacgga agaggaagaa ttctacctga gttcgccgta     360
aagcgcccgc cctctcgcct ctacgcttcc agttgcggct tattacgtca cagtaattgc     420
tgtaccaagg tcagaatcgc cacctgaggc ctgaatatca gcgtaagata gtgtccaaag     480
cagtcttaag aagaggtccc attaccccac tctttccgcc ctaatggagt cctccagttt     540
```

```
aggtaaataa aaggattgtt gggaggtgga gggaaagaac tactatttcc aacatgcatt      600
gcggaacgaa aggccttggc cacactgttc cttggaaact gtagtcttat ggagaggaac      660
atccaatacc aaagcgggca caattctcac ggaaatccag tggatagatt ggagacctcc      720
gcgggcttat acatgtcaac agtaatattg ggttgttatg ttctcctatc ttgagagcag      780
agactaggcc aaaaaaagat ataggaagac tacgattccc atccagcccc acgagtctcg      840
ggcaagtagt cctctaaggt cagtggcctg cggggacgca gtgggcgccg aatttgcctg      900
gggaagggga aatccctctc tggtcacatc tgcgcactcc tagttccgcc ctcagcatc      960 aatgtttgtt attgttgttc gggttcaggt tgcttctgcc ccgcccatc gacgcaatct      1020 ccaccaatca atggcgtggt cgttttgagg acaagtggt gagagccaat catcttggcg      1080
aacactcgga gaaacagggg actagttact gtctttatcc gccatgttag attcacccca      1140
cagggatagc ggcagagccg gtagcggacg gtccttgcat tggcctccgg caggcgcccc      1200 ccggggggcgg gaagctggta aggaagcagc tgcggtt                              1237
```

<210> SEQ ID NO 49
<211> LENGTH: 1863
<212> TYPE: PRT
<213> ORGANISM: Homo sapiens
<220> FEATURE:
<221> NAME/KEY: misc_feature
<222> LOCATION: (1472)
<223> OTHER INFORMATION: Xaa=any amino acid

<400> SEQUENCE: 49

```
Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220
```

-continued

```
Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
                260                 265                 270

Pro Cys Gly Thr Asn Thr His Ala Ser Ser Leu Gln His Glu Asn Ser
            275                 280                 285

Ser Leu Leu Leu Thr Lys Asp Arg Met Asn Val Glu Lys Ala Glu Phe
        290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
370                 375                 380

Trp Phe Ser Arg Ser Asp Glu Leu Leu Gly Ser Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
                420                 425                 430

Ala Ser Asp Pro His Glu Ala Leu Ile Cys Lys Ser Asp Arg Val His
            435                 440                 445

Ser Lys Ser Val Glu Ser Asp Ile Glu Asp Lys Ile Phe Gly Lys Thr
        450                 455                 460

Tyr Arg Lys Lys Ala Ser Leu Pro Asn Leu Ser His Val Thr Glu Asn
465                 470                 475                 480

Leu Ile Ile Gly Ala Phe Val Ser Glu Pro Gln Ile Ile Gln Glu Arg
                485                 490                 495

Pro Leu Thr Asn Lys Leu Lys Arg Lys Arg Arg Pro Thr Ser Gly Leu
                500                 505                 510

His Pro Glu Asp Phe Ile Lys Lys Ala Asp Leu Ala Val Gln Lys Thr
            515                 520                 525

Pro Glu Met Ile Asn Gln Gly Thr Asn Gln Thr Glu Gln Asn Gly Gln
        530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
                580                 585                 590

Asn Glu Leu Glu Leu Asn Ile Met His Asn Ser Lys Ala Pro Lys Lys
            595                 600                 605

Asn Arg Leu Arg Arg Lys Ser Ser Thr Arg His Ile His Ala Leu Glu
        610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
```

-continued

```
                645                 650                 655
Gln Met Pro Val Arg His Ser Arg Asn Leu Gln Leu Met Glu Gly Lys
                660                 665                 670
Glu Pro Ala Thr Gly Ala Lys Lys Ser Asn Lys Pro Asn Glu Gln Thr
            675                 680                 685
Ser Lys Arg His Asp Ser Asp Thr Phe Pro Glu Leu Lys Leu Thr Asn
        690                 695                 700
Ala Pro Gly Ser Phe Thr Lys Cys Ser Asn Thr Ser Glu Leu Lys Glu
705                 710                 715                 720
Phe Val Asn Pro Ser Leu Pro Arg Glu Glu Lys Glu Glu Lys Leu Glu
                725                 730                 735
Thr Val Lys Val Ser Asn Asn Ala Glu Asp Pro Lys Asp Leu Met Leu
            740                 745                 750
Ser Gly Glu Arg Val Leu Gln Thr Glu Arg Ser Val Glu Ser Ser Ser
        755                 760                 765
Ile Ser Leu Val Pro Gly Thr Asp Tyr Gly Thr Gln Glu Ser Ile Ser
    770                 775                 780
Leu Leu Glu Val Ser Thr Leu Gly Lys Ala Lys Thr Glu Pro Asn Lys
785                 790                 795                 800
Cys Val Ser Gln Cys Ala Ala Phe Glu Asn Pro Lys Gly Leu Ile His
                805                 810                 815
Gly Cys Ser Lys Asp Asn Arg Asn Asp Thr Glu Gly Phe Lys Tyr Pro
            820                 825                 830
Leu Gly His Glu Val Asn His Ser Arg Glu Thr Ser Ile Glu Met Glu
        835                 840                 845
Glu Ser Glu Leu Asp Ala Gln Tyr Leu Gln Asn Thr Phe Lys Val Ser
    850                 855                 860
Lys Arg Gln Ser Phe Ala Pro Phe Ser Asn Pro Gly Asn Ala Glu Glu
865                 870                 875                 880
Glu Cys Ala Thr Phe Ser Ala His Ser Gly Ser Leu Lys Lys Gln Ser
                885                 890                 895
Pro Lys Val Thr Phe Glu Cys Glu Gln Lys Glu Glu Asn Gln Gly Lys
            900                 905                 910
Asn Glu Ser Asn Ile Lys Pro Val Gln Thr Val Asn Ile Thr Ala Gly
        915                 920                 925
Phe Pro Val Val Gly Gln Lys Asp Lys Pro Val Asp Asn Ala Lys Cys
    930                 935                 940
Ser Ile Lys Gly Gly Ser Arg Phe Cys Leu Ser Ser Gln Phe Arg Gly
945                 950                 955                 960
Asn Glu Thr Gly Leu Ile Thr Pro Asn Lys His Gly Leu Leu Gln Asn
                965                 970                 975
Pro Tyr Arg Ile Pro Pro Leu Phe Pro Ile Lys Ser Phe Val Lys Thr
            980                 985                 990
Lys Cys Lys Lys Asn Leu Leu Glu Glu Asn Phe Glu Glu His Ser Met
        995                 1000                1005
Ser Pro Glu Arg Glu Met Gly Asn Glu Asn Ile Pro Ser Thr Val Ser
    1010                1015                1020
Thr Ile Ser Arg Asn Asn Ile Arg Glu Asn Val Phe Lys Glu Ala Ser
1025                1030                1035                1040
Ser Ser Asn Ile Asn Glu Val Gly Ser Ser Thr Asn Glu Val Gly Ser
                1045                1050                1055
Ser Ile Asn Glu Ile Gly Ser Ser Asp Glu Asn Ile Gln Ala Glu Leu
            1060                1065                1070
```

```
Gly Arg Asn Arg Gly Pro Lys Leu Asn Ala Met Leu Arg Leu Gly Val
        1075                1080                1085
Leu Gln Pro Glu Val Tyr Lys Gln Ser Leu Pro Gly Ser Asn Cys Lys
        1090                1095                1100
His Pro Glu Ile Lys Lys Gln Glu Tyr Glu Val Val Gln Thr Val
1105                1110                1115                1120
Asn Thr Asp Phe Ser Pro Tyr Leu Ile Ser Asp Asn Leu Glu Gln Pro
                1125                1130                1135
Met Gly Ser Ser His Ala Ser Gln Val Cys Ser Glu Thr Pro Asp Asp
            1140                1145                1150
Leu Leu Asp Asp Gly Glu Ile Lys Glu Asp Thr Ser Phe Ala Glu Asn
        1155                1160                1165
Asp Ile Lys Glu Ser Ser Ala Val Phe Ser Lys Ser Val Gln Lys Gly
        1170                1175                1180
Glu Leu Ser Arg Ser Pro Ser Pro Phe Thr His Thr His Leu Ala Gln
1185                1190                1195                1200
Gly Tyr Arg Arg Gly Ala Lys Lys Leu Glu Ser Ser Glu Glu Asn Leu
                1205                1210                1215
Ser Ser Glu Asp Glu Glu Leu Pro Cys Phe Gln His Leu Leu Phe Gly
            1220                1225                1230
Lys Val Asn Asn Ile Pro Ser Gln Ser Thr Arg His Ser Thr Val Ala
        1235                1240                1245
Thr Glu Cys Leu Ser Lys Asn Thr Glu Glu Asn Leu Leu Ser Leu Lys
        1250                1255                1260
Asn Ser Leu Asn Asp Cys Ser Asn Gln Val Ile Leu Ala Lys Ala Ser
1265                1270                1275                1280
Gln Glu His His Leu Ser Glu Glu Thr Lys Cys Ser Ala Ser Leu Phe
                1285                1290                1295
Ser Ser Gln Cys Ser Glu Leu Glu Asp Leu Thr Ala Asn Thr Asn Thr
            1300                1305                1310
Gln Asp Pro Phe Leu Ile Gly Ser Ser Lys Gln Met Arg His Gln Ser
        1315                1320                1325
Glu Ser Gln Gly Val Gly Leu Ser Asp Lys Glu Leu Val Ser Asp Asp
        1330                1335                1340
Glu Glu Arg Gly Thr Gly Leu Glu Glu Asn Asn Gln Glu Glu Gln Ser
1345                1350                1355                1360
Met Asp Ser Asn Leu Gly Glu Ala Ala Ser Gly Cys Glu Ser Glu Thr
                1365                1370                1375
Ser Val Ser Glu Asp Cys Ser Gly Leu Ser Ser Gln Ser Asp Ile Leu
            1380                1385                1390
Thr Thr Gln Gln Arg Asp Thr Met Gln His Asn Leu Ile Lys Leu Gln
        1395                1400                1405
Gln Glu Met Ala Glu Leu Glu Ala Val Leu Glu Gln His Gly Ser Gln
        1410                1415                1420
Pro Ser Asn Ser Tyr Pro Ser Ile Ile Ser Asp Ser Ser Ala Leu Glu
1425                1430                1435                1440
Asp Leu Arg Asn Pro Glu Gln Ser Thr Ser Glu Lys Val Leu Gln Thr
                1445                1450                1455
Ser Gln Lys Ser Ser Glu Tyr Pro Ile Ser Gln Asn Pro Glu Gly Xaa
            1460                1465                1470
Ser Ala Asp Lys Phe Glu Val Ser Ala Asp Ser Ser Thr Ser Lys Asn
        1475                1480                1485
```

-continued

```
Lys Glu Pro Gly Val Glu Arg Ser Ser Pro Ser Lys Cys Pro Ser Leu
    1490                1495                1500

Asp Asp Arg Trp Tyr Met His Ser Cys Ser Gly Ser Leu Gln Asn Arg
1505                1510                1515                1520

Asn Tyr Pro Pro Gln Glu Leu Ile Lys Val Val Asp Val Glu Glu
            1525                1530                1535

Gln Gln Leu Glu Glu Ser Gly Pro His Asp Leu Thr Glu Thr Ser Tyr
        1540                1545                1550

Leu Pro Arg Gln Asp Leu Glu Gly Thr Pro Tyr Leu Glu Ser Gly Ile
        1555                1560                1565

Ser Leu Phe Ser Asp Asp Pro Glu Ser Asp Pro Ser Glu Asp Arg Ala
    1570                1575                1580

Pro Glu Ser Ala Arg Val Gly Asn Ile Pro Ser Ser Thr Ser Ala Leu
1585                1590                1595                1600

Lys Val Pro Gln Leu Lys Val Ala Glu Ser Ala Gln Ser Pro Ala Ala
            1605                1610                1615

Ala His Thr Thr Asp Thr Ala Gly Tyr Asn Ala Met Glu Glu Ser Val
        1620                1625                1630

Ser Arg Glu Lys Pro Glu Leu Thr Ala Ser Thr Glu Arg Val Asn Lys
        1635                1640                1645

Arg Met Ser Met Val Val Ser Gly Leu Thr Pro Glu Glu Phe Met Leu
        1650                1655                1660

Val Tyr Lys Phe Ala Arg Lys His His Ile Thr Leu Thr Asn Leu Ile
1665                1670                1675                1680

Thr Glu Glu Thr Thr His Val Val Met Lys Thr Asp Ala Glu Phe Val
            1685                1690                1695

Cys Glu Arg Thr Leu Lys Tyr Phe Leu Gly Ile Ala Gly Gly Lys Trp
        1700                1705                1710

Val Val Ser Tyr Phe Trp Val Thr Gln Ser Ile Lys Glu Arg Lys Met
        1715                1720                1725

Leu Asn Glu His Asp Phe Glu Val Arg Gly Asp Val Val Asn Gly Arg
        1730                1735                1740

Asn His Gln Gly Pro Lys Arg Ala Arg Glu Ser Gln Asp Arg Lys Ile
1745                1750                1755                1760

Phe Arg Gly Leu Glu Ile Cys Cys Tyr Gly Pro Phe Thr Asn Met Pro
            1765                1770                1775

Thr Asp Gln Leu Glu Trp Met Val Gln Leu Cys Gly Ala Ser Val Val
        1780                1785                1790

Lys Glu Leu Ser Ser Phe Thr Leu Gly Thr Gly Val His Pro Ile Val
            1795                1800                1805

Val Val Gln Pro Asp Ala Trp Thr Glu Asp Asn Gly Phe His Ala Ile
        1810                1815                1820

Gly Gln Met Cys Glu Ala Pro Val Val Thr Arg Glu Trp Val Leu Asp
1825                1830                1835                1840

Ser Val Ala Leu Tyr Gln Cys Gln Glu Leu Asp Thr Tyr Leu Ile Pro
            1845                1850                1855

Gln Ile Pro His Ser His Tyr
            1860

<210> SEQ ID NO 50
<211> LENGTH: 17
<212> TYPE: DNA
<213> ORGANISM: Artificial Sequence
<220> FEATURE:
<223> OTHER INFORMATION: Synthesized PCR Primer
```

<400> SEQUENCE: 50
caattgggca gatgtgt                                                17

<210> SEQ ID NO 51
<211> LENGTH: 20
<212> TYPE: DNA
<213> ORGANISM: Artificial Sequence
<220> FEATURE:
<223> OTHER INFORMATION: Synthesized PCR Primer

<400> SEQUENCE: 51
ctgggggatc tggggtatca                                             20

<210> SEQ ID NO 52
<211> LENGTH: 18
<212> TYPE: DNA
<213> ORGANISM: Artificial Sequence
<220> FEATURE:
<223> OTHER INFORMATION: Synthesized PCR Primer

<400> SEQUENCE: 52
aagagcagat aaatccat                                               18

<210> SEQ ID NO 53
<211> LENGTH: 18
<212> TYPE: DNA
<213> ORGANISM: Artificial Sequence
<220> FEATURE:
<223> OTHER INFORMATION: Synthesized PCR Primer

<400> SEQUENCE: 53
atggatttat ctgctctt                                               18

<210> SEQ ID NO 54
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 54
gatgagttcg tgtccgtaca actgg                                       25

<210> SEQ ID NO 55
<211> LENGTH: 25
<212> TYPE: DNA
<213> ORGANISM: Artificial Sequence
<220> FEATURE:
<223> OTHER INFORMATION: Synthesized PCR Primer

<400> SEQUENCE: 55
ggttatcgaa atcagccaca gcgcc                                       25

<210> SEQ ID NO 56
<211> LENGTH: 38
<212> TYPE: DNA
<213> ORGANISM: Homo sapiens

<400> SEQUENCE: 56
ttctcctgac cactaatggg agccaattca caattcac                         38

<210> SEQ ID NO 57
<211> LENGTH: 40
<212> TYPE: DNA

-continued

```
<213> ORGANISM: Homo sapiens

<400> SEQUENCE: 57
taagtgacta aagtaagtta aacttgtgta gactaagcat                40

<210> SEQ ID NO 58
<211> LENGTH: 35
<212> TYPE: DNA
<213> ORGANISM: Mesocricetus auratus

<400> SEQUENCE: 58
ttctgttcac cactgatggc agctaatgaa aatgc                     35

<210> SEQ ID NO 59
<211> LENGTH: 27
<212> TYPE: DNA
<213> ORGANISM: Mesocricetus auratus

<400> SEQUENCE: 59
aagtgactca gaagttagtg ttagcat                              27

<210> SEQ ID NO 60
<211> LENGTH: 34
<212> TYPE: DNA
<213> ORGANISM: Mesocricetus auratus

<400> SEQUENCE: 60
gggggatcca tagttctaga gcggccgcca ccgc                      34

<210> SEQ ID NO 61
<211> LENGTH: 37
<212> TYPE: DNA
<213> ORGANISM: Mesocricetus auratus

<400> SEQUENCE: 61
tggagctcca gcttttgttc cctttagtga gggttaa                   37
```